United States Patent
Meridew et al.

(10) Patent No.: US 8,608,749 B2
(45) Date of Patent: Dec. 17, 2013

(54) PATIENT-SPECIFIC ACETABULAR GUIDES AND ASSOCIATED INSTRUMENTS

(75) Inventors: Jason D. Meridew, Warsaw, IN (US); Tony Siebeneck, Mentone, IN (US); Tyler D. Witt, Fond du Lac, WI (US); Robert Metzger, Wakarusa, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 13/041,469

(22) Filed: Mar. 7, 2011

(65) Prior Publication Data

US 2011/0184419 A1    Jul. 28, 2011

Related U.S. Application Data

(63) Continuation-in-part of application No. 12/973,214, filed on Dec. 20, 2010, which is a continuation-in-part of application No. 12/955,361, filed on Nov. 29, 2010, which is a continuation-in-part of application No. 12/938,905, filed on Nov. 3, 2010, and a continuation-in-part of application No. 12/938,913, filed on Nov. 3, 2010, said application No. 12/938,905 is a continuation-in-part of application No. 12/893,306, filed on Sep. 29, 2010, said application No. 12/938,913 is a continuation-in-part of application No. 12/893,306, which is a continuation-in-part of (Continued)

(51) Int. Cl.
    *A61F 2/34*    (2006.01)
(52) U.S. Cl.
    USPC ......................... 606/91; 623/22.23
(58) Field of Classification Search
    USPC .......................... 623/22.11–23.38
    See application file for complete search history.

(56) References Cited

U.S. PATENT DOCUMENTS

| 1,480,285 A | 1/1924 | Moore |
| 2,181,746 A | 11/1939 | Siebrandt |

(Continued)

FOREIGN PATENT DOCUMENTS

| CA | 2447694 A1 | 12/2002 |
| CA | 2501041 A1 | 4/2004 |

(Continued)

OTHER PUBLICATIONS

"Amazing Precision. Beautiful Results. The next evolution of MAKOplasty® is here," brochure. (Feb. 2009) MAKO Surgical Corp. 6 pages.

(Continued)

*Primary Examiner* — David Isabella
*Assistant Examiner* — Ann Schillinger
(74) *Attorney, Agent, or Firm* — Harness, Dickey

(57) ABSTRACT

A method for preparing a joint surface of a patient for an implant, such as, for example, an acetabular implant for a hip joint. According to the method, a patient-specific guide is attached to a complementary joint surface of the patient. The patient-specific guide includes a guiding element oriented along a patient-specific alignment axis. The alignment axis is determined during a preoperative plan of the patient for implant alignment. A shaft of a guiding tool is removably coupled to the guiding element of the guide. A three-dimensional orientation device is removably attached to the shaft of the guiding tool. A position of a bubble of the orientation device is marked with a mark on an outer transparent surface of the orientation device while the guiding tool is oriented along the alignment axis. The marked orientation device can be used for aligning other instruments during the procedure.

16 Claims, 12 Drawing Sheets

Related U.S. Application Data

(63) application No. 12/888,005, filed on Sep. 22, 2010, which is a continuation-in-part of application No. 12/714,023, filed on Feb. 26, 2010, which is a continuation-in-part of application No. 12/571,969, filed on Oct. 1, 2009, which is a continuation-in-part of application No. 12/486,992, filed on Jun. 18, 2009, and a continuation-in-part of application No. 12/389,901,filed on Feb. 20, 2009, which is a continuation-in-part of application No. 12/211,407, filed on Sep. 16, 2008, which is a continuation-in-part of application No. 12/039,849, filed on Feb. 29, 2008, which is a continuation-in-part of application No. 11/756,057, filed on May 31, 2007, and a continuation-in-part of application No. 11/971,390, filed on Jan. 9, 2008, which is a continuation-in-part of application No. 11/363,548, filed on Feb. 27, 2006, now Pat. No. 7,780,672, said application No. 12/039,849 is a continuation-in-part of application No. 12/025,414, filed on Feb. 4, 2008, application No. 13/041,469, which is a continuation-in-part of application No. 12/872,663, filed on Aug. 31, 2010, and a continuation-in-part of application No. 12/483,807, filed on Jun. 12, 2009, which is a continuation-in-part of application No. 12/371,096, filed on Feb. 13, 2009, which is a continuation-in-part of application No. 12/103,824, filed on Apr. 16, 2008, application No. 13/041,469, which is a continuation-in-part of application No. 12/103,834, filed on Apr. 16, 2008, and a continuation-in-part of application No. 12/978,069, filed on Dec. 23, 2010, which is a continuation-in-part of application No. 12/973,214.

(60) Provisional application No. 61/446,660, filed on Feb. 25, 2011, provisional application No. 60/953,620, filed on Aug. 2, 2007, provisional application No. 60/947,813, filed on Jul. 3, 2007, provisional application No. 60/911,297, filed on Apr. 12, 2007, provisional application No. 60/892,349, filed on Mar. 1, 2007, provisional application No. 60/812,694, filed on Jun. 9, 2006, provisional application No. 60/953,637, filed on Aug. 2, 2007, provisional application No. 61/310,752, filed on Mar. 5, 2010, provisional application No. 60/912,178, filed on Apr. 17, 2007.

(56) References Cited

U.S. PATENT DOCUMENTS

| | | | |
|---|---|---|---|
| 2,407,845 | A | 9/1946 | Nemeyer |
| 2,618,913 | A | 11/1952 | Plancon et al. |
| 2,910,978 | A | 11/1959 | Urist |
| 3,840,904 | A | 10/1974 | Tronzo |
| 4,246,895 | A | 1/1981 | Rehder |
| 4,306,866 | A | 12/1981 | Weissman |
| 4,324,006 | A | 4/1982 | Charnley |
| 4,421,112 | A | 12/1983 | Mains et al. |
| 4,436,684 | A | 3/1984 | White |
| 4,475,549 | A | 10/1984 | Oh |
| 4,506,393 | A | 3/1985 | Murphy |
| 4,524,766 | A | 6/1985 | Petersen |
| 4,619,658 | A | 10/1986 | Pappas et al. |
| 4,621,630 | A | 11/1986 | Kenna |
| 4,632,111 | A | 12/1986 | Roche |
| 4,633,862 | A | 1/1987 | Petersen |
| 4,663,720 | A | 5/1987 | Duret et al. |
| 4,695,283 | A | 9/1987 | Aldinger |
| 4,696,292 | A | 9/1987 | Heiple |
| 4,703,751 | A | 11/1987 | Pohl |
| 4,704,686 | A | 11/1987 | Aldinger |
| 4,719,907 | A | 1/1988 | Banko et al. |
| 4,721,104 | A | 1/1988 | Kaufman et al. |
| 4,722,330 | A | 2/1988 | Russell et al. |
| 4,778,474 | A | 10/1988 | Homsy |
| 4,800,874 | A | 1/1989 | David et al. |
| 4,821,213 | A | 4/1989 | Cline et al. |
| 4,822,365 | A | 4/1989 | Walker et al. |
| 4,841,975 | A | 6/1989 | Woolson |
| 4,846,161 | A | 7/1989 | Roger |
| 4,871,975 | A | 10/1989 | Nawata et al. |
| 4,893,619 | A | 1/1990 | Dale et al. |
| 4,896,663 | A | 1/1990 | Vandewalls |
| 4,927,422 | A | 5/1990 | Engelhardt |
| 4,936,862 | A | 6/1990 | Walker et al. |
| 4,952,213 | A | 8/1990 | Bowman et al. |
| 4,959,066 | A | 9/1990 | Dunn et al. |
| 4,976,737 | A | 12/1990 | Leake |
| 4,979,949 | A | 12/1990 | Matsen, III et al. |
| 4,985,037 | A | 1/1991 | Petersen |
| 5,002,579 | A | 3/1991 | Copf et al. |
| 5,007,936 | A | 4/1991 | Woolson |
| 5,019,105 | A | 5/1991 | Wiley |
| 5,030,221 | A | 7/1991 | Buechel et al. |
| 5,041,117 | A | 8/1991 | Engelhardt |
| 5,053,037 | A | 10/1991 | Lackey |
| 5,053,039 | A | 10/1991 | Hofmann et al. |
| 5,086,401 | A | 2/1992 | Glassman et al. |
| 5,098,383 | A | 3/1992 | Hemmy et al. |
| 5,098,436 | A | 3/1992 | Ferrante et al. |
| 5,108,425 | A | 4/1992 | Hwang |
| 5,122,144 | A | 6/1992 | Bert et al. |
| 5,129,908 | A | 7/1992 | Petersen |
| 5,129,909 | A | 7/1992 | Sutherland |
| 5,133,760 | A | 7/1992 | Petersen et al. |
| 5,140,777 | A | 8/1992 | Ushiyama et al. |
| 5,150,304 | A | 9/1992 | Berchem et al. |
| 5,176,684 | A | 1/1993 | Ferrante et al. |
| 5,176,711 | A | 1/1993 | Grimes |
| 5,246,444 | A | 9/1993 | Schreiber |
| 5,258,032 | A | 11/1993 | Bertin |
| 5,261,915 | A | 11/1993 | Durlacher et al. |
| 5,274,565 | A | 12/1993 | Reuben |
| 5,299,288 | A | 3/1994 | Glassman et al. |
| 5,300,077 | A | 4/1994 | Howell |
| 5,320,625 | A | 6/1994 | Bertin |
| 5,342,366 | A | 8/1994 | Whiteside et al. |
| 5,344,423 | A | 9/1994 | Dietz et al. |
| 5,360,446 | A | 11/1994 | Kennedy |
| 5,364,402 | A | 11/1994 | Mumme et al. |
| 5,368,858 | A | 11/1994 | Hunziker |
| 5,370,692 | A | 12/1994 | Fink et al. |
| 5,370,699 | A | 12/1994 | Hood et al. |
| 5,405,395 | A | 4/1995 | Coates |
| 5,408,409 | A | 4/1995 | Glassman et al. |
| 5,415,662 | A | 5/1995 | Ferrante et al. |
| 5,417,694 | A | 5/1995 | Marik et al. |
| 5,438,263 | A | 8/1995 | Dworkin et al. |
| 5,440,496 | A | 8/1995 | Andersson et al. |
| 5,448,489 | A | 9/1995 | Reuben |
| 5,449,360 | A | 9/1995 | Schreiber |
| 5,452,407 | A | 9/1995 | Crook |
| 5,454,816 | A | 10/1995 | Ashby |
| 5,472,415 | A | 12/1995 | King et al. |
| 5,474,559 | A | 12/1995 | Bertin et al. |
| 5,490,854 | A | 2/1996 | Fisher et al. |
| 5,496,324 | A | 3/1996 | Barnes |
| 5,507,833 | A | 4/1996 | Bohn |
| 5,514,519 | A | 5/1996 | Neckers |
| 5,520,695 | A | 5/1996 | Luckman |
| 5,527,317 | A | 6/1996 | Ashby et al. |
| 5,539,649 | A | 7/1996 | Walsh et al. |
| 5,540,695 | A | 7/1996 | Levy |
| 5,549,688 | A | 8/1996 | Ries et al. |
| 5,554,190 | A | 9/1996 | Draenert |
| 5,560,096 | A | 10/1996 | Stephens |
| 5,571,110 | A | 11/1996 | Matsen, III et al. |

(56) References Cited

U.S. PATENT DOCUMENTS

| | | |
|---|---|---|
| 5,578,037 A | 11/1996 | Sanders et al. |
| 5,595,703 A | 1/1997 | Swaelens et al. |
| 5,607,431 A | 3/1997 | Dudasik et al. |
| 5,613,969 A | 3/1997 | Jenkins, Jr. |
| 5,620,448 A | 4/1997 | Puddu |
| 5,634,927 A | 6/1997 | Houston et al. |
| 5,641,323 A | 6/1997 | Caldarise |
| 5,658,294 A | 8/1997 | Sederholm |
| 5,662,656 A | 9/1997 | White |
| 5,671,018 A | 9/1997 | Ohara et al. |
| 5,677,107 A | 10/1997 | Neckers |
| 5,681,354 A | 10/1997 | Eckhoff |
| 5,682,886 A | 11/1997 | Delp et al. |
| 5,690,635 A | 11/1997 | Matsen, III et al. |
| 5,702,460 A | 12/1997 | Carls et al. |
| 5,704,941 A | 1/1998 | Jacober et al. |
| 5,722,978 A | 3/1998 | Jenkins, Jr. |
| 5,725,376 A | 3/1998 | Poirier |
| 5,725,593 A | 3/1998 | Caracciolo |
| 5,735,277 A | 4/1998 | Schuster |
| 5,748,767 A | 5/1998 | Raab |
| 5,749,875 A | 5/1998 | Puddu |
| 5,749,876 A | 5/1998 | Duvillier et al. |
| 5,762,125 A | 6/1998 | Mastrorio |
| 5,768,134 A | 6/1998 | Swaelens et al. |
| 5,769,092 A | 6/1998 | Williamson, Jr. |
| 5,786,217 A | 7/1998 | Tubo et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,860,981 A | 1/1999 | Bertin et al. |
| 5,871,018 A | 2/1999 | Delp et al. |
| 5,876,456 A | 3/1999 | Sederholm et al. |
| 5,879,398 A | 3/1999 | Swarts et al. |
| 5,879,402 A | 3/1999 | Lawes et al. |
| 5,879,404 A | 3/1999 | Bateman et al. |
| 5,880,976 A | 3/1999 | DiGioia, III et al. |
| 5,885,297 A | 3/1999 | Matsen, III |
| 5,885,298 A | 3/1999 | Herrington et al. |
| 5,895,389 A | 4/1999 | Schenk et al. |
| 5,899,907 A | 5/1999 | Johnson |
| 5,901,060 A | 5/1999 | Schall et al. |
| 5,911,724 A | 6/1999 | Wehrli |
| 5,921,988 A | 7/1999 | Legrand |
| 5,925,049 A | 7/1999 | Gustilo et al. |
| 5,925,077 A | 7/1999 | Williamson et al. |
| 5,942,370 A | 8/1999 | Neckers |
| 5,967,777 A | 10/1999 | Klein et al. |
| 5,976,149 A | 11/1999 | Masini |
| 5,980,526 A | 11/1999 | Johnson et al. |
| 6,033,415 A | 3/2000 | Mittelstadt et al. |
| 6,059,789 A | 5/2000 | Dinger et al. |
| 6,059,833 A | 5/2000 | Doets |
| 6,086,593 A | 7/2000 | Bonutti |
| 6,120,510 A | 9/2000 | Albrektsson et al. |
| 6,120,544 A | 9/2000 | Grundei et al. |
| 6,126,690 A | 10/2000 | Ateshian et al. |
| 6,132,469 A | 10/2000 | Schroeder |
| 6,136,033 A | 10/2000 | Suemer |
| 6,156,069 A | 12/2000 | Amstutz |
| 6,161,080 A | 12/2000 | Aouni-Ateshian et al. |
| 6,187,010 B1 | 2/2001 | Masini |
| 6,195,615 B1 | 2/2001 | Lysen |
| 6,203,546 B1 | 3/2001 | MacMahon |
| 6,205,411 B1 | 3/2001 | DiGioia, III et al. |
| 6,206,927 B1 | 3/2001 | Fell et al. |
| 6,254,604 B1 | 7/2001 | Howell |
| 6,258,097 B1 | 7/2001 | Cook et al. |
| 6,264,698 B1 | 7/2001 | Lawes et al. |
| 6,273,891 B1 | 8/2001 | Masini |
| 6,290,727 B1 | 9/2001 | Otto et al. |
| 6,293,971 B1 | 9/2001 | Nelson et al. |
| 6,312,258 B1 | 11/2001 | Ashman |
| 6,312,473 B1 | 11/2001 | Oshida |
| 6,319,285 B1 | 11/2001 | Chamier et al. |
| 6,325,829 B1 | 12/2001 | Schmotzer |
| 6,343,987 B2 | 2/2002 | Hayama et al. |
| 6,354,011 B1 | 3/2002 | Albrecht |
| 6,379,299 B1 | 4/2002 | Borodulin et al. |
| 6,383,228 B1 | 5/2002 | Schmotzer |
| 6,391,251 B1 | 5/2002 | Keicher et al. |
| 6,395,005 B1 | 5/2002 | Lovell |
| 6,416,553 B1 | 7/2002 | White et al. |
| 6,427,698 B1 | 8/2002 | Yoon |
| 6,459,948 B1 | 10/2002 | Ateshian et al. |
| 6,463,351 B1 | 10/2002 | Clynch |
| 6,475,243 B1 | 11/2002 | Sheldon et al. |
| 6,482,236 B2 | 11/2002 | Habecker |
| 6,488,715 B1 | 12/2002 | Pope et al. |
| 6,503,255 B1 | 1/2003 | Albrektsson et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,520,964 B2 | 2/2003 | Tallarida et al. |
| 6,533,737 B1 | 3/2003 | Brosseau et al. |
| 6,547,823 B2 | 4/2003 | Scarborough et al. |
| 6,554,837 B1 | 4/2003 | Hauri et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,591,581 B2 | 7/2003 | Schmieding |
| 6,605,293 B1 | 8/2003 | Giordano et al. |
| 6,622,567 B1 | 9/2003 | Hamel et al. |
| 6,629,999 B1 | 10/2003 | Serafin, Jr. |
| 6,641,617 B1 | 11/2003 | Merrill et al. |
| 6,682,566 B2 | 1/2004 | Draenert |
| 6,682,567 B1 | 1/2004 | Schroeder |
| 6,696,073 B2 | 2/2004 | Boyce et al. |
| 6,697,664 B2 | 2/2004 | Kienzle, III et al. |
| 6,701,174 B1 | 3/2004 | Krause et al. |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,749,638 B1 | 6/2004 | Saladino |
| 6,750,653 B1 | 6/2004 | Zou et al. |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,823,871 B2 | 11/2004 | Schmieding |
| 6,827,723 B2 | 12/2004 | Carson |
| 6,887,247 B1 | 5/2005 | Couture et al. |
| 6,905,514 B2 | 6/2005 | Carignan et al. |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |
| 6,966,932 B1 | 11/2005 | Schroeder |
| 6,990,220 B2 | 1/2006 | Ellis et al. |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | McKinnon |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,121,832 B2 | 10/2006 | Hsieh et al. |
| 7,141,053 B2 | 11/2006 | Rosa et al. |

(56) References Cited

U.S. PATENT DOCUMENTS

| | | |
|---|---|---|
| 7,169,185 B2 | 1/2007 | Sidebotham |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | DiSilvestro et al. |
| 7,220,264 B1 | 5/2007 | Hershberger |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,207 B1 | 2/2008 | Smith |
| 7,335,231 B2 | 2/2008 | McLean |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,392,076 B2 | 6/2008 | Moctezuma de La Barrera |
| 7,427,200 B2 | 9/2008 | Noble et al. |
| 7,427,272 B2 | 9/2008 | Richard et al. |
| 7,468,075 B2 | 12/2008 | Lang et al. |
| 7,474,223 B2 | 1/2009 | Nycz et al. |
| 7,488,325 B2 | 2/2009 | Qian |
| 7,494,510 B2 | 2/2009 | Zweymuller |
| 7,517,365 B2 | 4/2009 | Carignan et al. |
| 7,527,631 B2 | 5/2009 | Maroney et al. |
| 7,534,263 B2 | 5/2009 | Burdulis, Jr. et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kelman |
| 7,601,155 B2 | 10/2009 | Petersen |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-Schaffer et al. |
| 7,651,501 B2 | 1/2010 | Penenberg et al. |
| 7,670,345 B2 | 3/2010 | Plassky et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,704,253 B2 | 4/2010 | Bastian et al. |
| 7,723,395 B2 | 5/2010 | Ringeisen et al. |
| 7,780,672 B2 | 8/2010 | Metzger et al. |
| 7,780,740 B2 | 8/2010 | Steinberg |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,879,109 B2 | 2/2011 | Borden et al. |
| 7,892,261 B2 | 2/2011 | Bonutti |
| 7,896,921 B2 | 3/2011 | Smith et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,993,353 B2 | 8/2011 | Rossner et al. |
| 8,062,301 B2 | 11/2011 | Ammann et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,133,230 B2 | 3/2012 | Stevens et al. |
| 8,133,234 B2 | 3/2012 | Meridew et al. |
| 8,137,406 B2 | 3/2012 | Novak et al. |
| 8,167,951 B2 | 5/2012 | Ammann et al. |
| 8,170,641 B2 | 5/2012 | Belcher |
| 8,182,489 B2 | 5/2012 | Horacek |
| 8,192,441 B2 | 6/2012 | Collazo |
| 8,192,495 B2 | 6/2012 | Simpson et al. |
| 8,211,112 B2 | 7/2012 | Novak et al. |
| 8,241,292 B2 | 8/2012 | Collazo |
| 8,241,293 B2 | 8/2012 | Stone et al. |
| 8,265,790 B2 | 9/2012 | Amiot et al. |
| 8,282,646 B2 | 10/2012 | Schoenefeld et al. |
| 8,298,237 B2 | 10/2012 | Schoenefeld et al. |
| 8,303,596 B2 | 11/2012 | Plassky et al. |
| 8,333,772 B2 | 12/2012 | Fox et al. |
| 8,355,773 B2 | 1/2013 | Leitner et al. |
| 2001/0005797 A1 | 6/2001 | Barlow et al. |
| 2001/0011190 A1 | 8/2001 | Park |
| 2001/0054478 A1 | 12/2001 | Watanabe et al. |
| 2002/0007294 A1 | 1/2002 | Bradbury et al. |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0107522 A1 | 8/2002 | Picard et al. |
| 2002/0120342 A1 | 8/2002 | Gibbs |
| 2002/0128872 A1 | 9/2002 | Giammattei |
| 2002/0147415 A1 | 10/2002 | Martelli |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0039676 A1 | 2/2003 | Boyce et al. |
| 2003/0055502 A1 | 3/2003 | Lang et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0212459 A1 | 11/2003 | Gibbs |
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0204644 A1 | 10/2004 | Tsougarakis et al. |
| 2004/0204760 A1 | 10/2004 | Fitz et al. |

(56) References Cited

U.S. PATENT DOCUMENTS

| | | |
|---|---|---|
| 2004/0212586 A1 | 10/2004 | Denny |
| 2004/0220583 A1 | 11/2004 | Pieczynski et al. |
| 2004/0225369 A1 | 11/2004 | Lakin et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0021148 A1 | 1/2005 | Gibbs |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | de la Barrera |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0148843 A1 | 7/2005 | Roose |
| 2005/0149042 A1 | 7/2005 | Metzger |
| 2005/0171545 A1 | 8/2005 | Walsh et al. |
| 2005/0177245 A1 | 8/2005 | Leatherbury et al. |
| 2005/0203536 A1 | 9/2005 | Laffargue et al. |
| 2005/0203540 A1 | 9/2005 | Broyles |
| 2005/0216305 A1 | 9/2005 | Funderud |
| 2005/0222573 A1 | 10/2005 | Branch et al. |
| 2005/0228393 A1 | 10/2005 | Williams et al. |
| 2005/0234461 A1 | 10/2005 | Burdulis et al. |
| 2005/0234465 A1 | 10/2005 | McCombs et al. |
| 2005/0234468 A1 | 10/2005 | Carson |
| 2005/0240195 A1 | 10/2005 | Axelson et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro et al. |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady et al. |
| 2006/0100832 A1 | 5/2006 | Bowman |
| 2006/0111722 A1 | 5/2006 | Bouadi |
| 2006/0122616 A1 | 6/2006 | Bennett et al. |
| 2006/0136058 A1 | 6/2006 | Pietrzak |
| 2006/0142657 A1 | 6/2006 | Quaid et al. |
| 2006/0155380 A1 | 7/2006 | Clemow et al. |
| 2006/0161167 A1 * | 7/2006 | Myers et al. ............ 606/91 |
| 2006/0172263 A1 | 8/2006 | Quadling et al. |
| 2006/0178497 A1 | 8/2006 | Gevaert et al. |
| 2006/0184177 A1 * | 8/2006 | Echeverri ............ 606/91 |
| 2006/0184250 A1 | 8/2006 | Bandoh et al. |
| 2006/0190086 A1 | 8/2006 | Clemow et al. |
| 2006/0195111 A1 | 8/2006 | Couture |
| 2006/0195194 A1 | 8/2006 | Gunther |
| 2006/0195198 A1 | 8/2006 | James |
| 2006/0198943 A1 | 9/2006 | Kumar |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak et al. |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0293681 A1 | 12/2006 | Claypool et al. |
| 2007/0015995 A1 | 1/2007 | Lang et al. |
| 2007/0016209 A1 | 1/2007 | Ammann et al. |
| 2007/0027680 A1 | 2/2007 | Ashley et al. |
| 2007/0066917 A1 | 3/2007 | Hodorek et al. |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0106391 A1 | 5/2007 | Ronk |
| 2007/0118055 A1 | 5/2007 | McCombs |
| 2007/0118138 A1 | 5/2007 | Seo et al. |
| 2007/0118243 A1 | 5/2007 | Schroeder et al. |
| 2007/0150068 A1 | 6/2007 | Dong et al. |
| 2007/0156066 A1 | 7/2007 | McGinley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones et al. |
| 2007/0198022 A1 | 8/2007 | Lang et al. |
| 2007/0203430 A1 | 8/2007 | Lang et al. |
| 2007/0203583 A1 | 8/2007 | Slone |
| 2007/0203605 A1 | 8/2007 | Melton et al. |
| 2007/0219562 A1 | 9/2007 | Slone et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor et al. |
| 2007/0239481 A1 | 10/2007 | DiSilvestro et al. |
| 2007/0244487 A1 | 10/2007 | Ammann et al. |
| 2007/0250169 A1 | 10/2007 | Lang |
| 2007/0250175 A1 | 10/2007 | Meridew et al. |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288029 A1 | 12/2007 | Justin et al. |
| 2007/0288030 A1 | 12/2007 | Metzger et al. |
| 2008/0009874 A1 | 1/2008 | Meridew et al. |
| 2008/0009952 A1 | 1/2008 | Hodge |
| 2008/0015599 A1 | 1/2008 | D'Alessio et al. |
| 2008/0015603 A1 | 1/2008 | Collazo |

(56) References Cited

U.S. PATENT DOCUMENTS

| | | |
|---|---|---|
| 2008/0015604 A1 | 1/2008 | Collazo |
| 2008/0015605 A1 | 1/2008 | Collazo |
| 2008/0021299 A1 | 1/2008 | Meulink |
| 2008/0021494 A1 | 1/2008 | Schmelzeisen-Redeker et al. |
| 2008/0021567 A1 | 1/2008 | Meulink et al. |
| 2008/0027563 A1 | 1/2008 | Johnson et al. |
| 2008/0033442 A1 | 2/2008 | Amiot et al. |
| 2008/0039850 A1 | 2/2008 | Rowley et al. |
| 2008/0051799 A1 | 2/2008 | Bonutti |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0097451 A1 | 4/2008 | Chen et al. |
| 2008/0112996 A1 | 5/2008 | Harlow et al. |
| 2008/0114370 A1 | 5/2008 | Schoenefeld |
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147073 A1 | 6/2008 | Ammann et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |
| 2008/0195099 A1 | 8/2008 | Minas |
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0221699 A1 | 9/2008 | Meridew et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0255674 A1 | 10/2008 | Rahaman et al. |
| 2008/0257363 A1 | 10/2008 | Schoenefeld et al. |
| 2008/0262500 A1 | 10/2008 | Collazo |
| 2008/0262624 A1 | 10/2008 | White et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2008/0294170 A1 | 11/2008 | O'Brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0024131 A1 | 1/2009 | Metzger et al. |
| 2009/0043556 A1 | 2/2009 | Axelson et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0082770 A1 | 3/2009 | Worner et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |
| 2009/0118736 A1 | 5/2009 | Kreuzer |
| 2009/0118769 A1 | 5/2009 | Sixto, Jr. et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0204225 A1 | 8/2009 | Meridew et al. |
| 2009/0209884 A1 | 8/2009 | Van Vorhis et al. |
| 2009/0209961 A1 | 8/2009 | Ferrante et al. |
| 2009/0210067 A1 | 8/2009 | Meridew |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez et al. |
| 2009/0234360 A1 | 9/2009 | Alexander |
| 2009/0248044 A1 | 10/2009 | Amiot et al. |
| 2009/0254093 A1 | 10/2009 | White et al. |
| 2009/0254367 A1 | 10/2009 | Belcher et al. |
| 2009/0259312 A1 | 10/2009 | Shterling et al. |
| 2009/0270868 A1 | 10/2009 | Park et al. |
| 2009/0274350 A1 | 11/2009 | Pavlovskaia et al. |
| 2009/0287217 A1 | 11/2009 | Ammann et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2010/0010493 A1 | 1/2010 | Dower |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0036404 A1 | 2/2010 | Yi et al. |
| 2010/0042105 A1 | 2/2010 | Park et al. |
| 2010/0049195 A1 | 2/2010 | Park et al. |
| 2010/0049327 A1 | 2/2010 | Isch et al. |
| 2010/0057088 A1 | 3/2010 | Shah |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0087829 A1 | 4/2010 | Metzger et al. |
| 2010/0094295 A1 | 4/2010 | Schnieders et al. |
| 2010/0105011 A1 | 4/2010 | Karkar et al. |
| 2010/0121334 A1 | 5/2010 | Couture et al. |
| 2010/0121335 A1 | 5/2010 | Penenberg et al. |
| 2010/0131073 A1 | 5/2010 | Meridew et al. |
| 2010/0136214 A1 | 6/2010 | Kumar |
| 2010/0137869 A1 | 6/2010 | Borja et al. |
| 2010/0137924 A1 | 6/2010 | Tuke et al. |
| 2010/0145343 A1 | 6/2010 | Johnson et al. |
| 2010/0145344 A1 | 6/2010 | Jordan et al. |
| 2010/0145466 A1 | 6/2010 | Slone |
| 2010/0152782 A1 | 6/2010 | Stone et al. |

(56) References Cited

U.S. PATENT DOCUMENTS

| | | |
|---|---|---|
| 2010/0160917 A1 | 6/2010 | Fitz et al. |
| 2010/0168752 A1 | 7/2010 | Edwards |
| 2010/0168754 A1 | 7/2010 | Fitz et al. |
| 2010/0168857 A1 | 7/2010 | Hatch |
| 2010/0179663 A1 | 7/2010 | Steinberg |
| 2010/0185202 A1 | 7/2010 | Lester et al. |
| 2010/0191244 A1 | 7/2010 | White et al. |
| 2010/0198224 A1 | 8/2010 | Metzger et al. |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0286789 A1 | 11/2010 | Meridew |
| 2010/0292743 A1 | 11/2010 | Singhal et al. |
| 2010/0305574 A1 | 12/2010 | Fitz et al. |
| 2010/0318088 A1 | 12/2010 | Warne et al. |
| 2010/0324692 A1 | 12/2010 | Uthgenannt et al. |
| 2011/0004317 A1 | 1/2011 | Hacking et al. |
| 2011/0009869 A1 | 1/2011 | Marino et al. |
| 2011/0015636 A1 | 1/2011 | Katrana et al. |
| 2011/0015639 A1 | 1/2011 | Metzger et al. |
| 2011/0015752 A1 | 1/2011 | Meridew |
| 2011/0015753 A1 | 1/2011 | Meridew |
| 2011/0022049 A1 | 1/2011 | Huebner et al. |
| 2011/0029091 A1 | 2/2011 | Bojarski et al. |
| 2011/0029116 A1 | 2/2011 | Jordan et al. |
| 2011/0035012 A1 | 2/2011 | Linares |
| 2011/0040303 A1 | 2/2011 | Iannotti |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0092804 A1 | 4/2011 | Schoenefeld et al. |
| 2011/0093086 A1 | 4/2011 | Witt et al. |
| 2011/0106254 A1 | 5/2011 | Abel et al. |
| 2011/0125264 A1 | 5/2011 | Bagga et al. |
| 2011/0130795 A1 | 6/2011 | Ball |
| 2011/0151027 A1 | 6/2011 | Clineff et al. |
| 2011/0151259 A1 | 6/2011 | Jarman-Smith et al. |
| 2011/0153025 A1 | 6/2011 | McMinn |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184424 A1 | 7/2011 | Isch et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0214279 A1 | 9/2011 | Park et al. |
| 2011/0218545 A1 | 9/2011 | Catanzarite et al. |
| 2011/0224674 A1 | 9/2011 | White et al. |
| 2011/0251617 A1 | 10/2011 | Ammann et al. |
| 2011/0257657 A1 | 10/2011 | Turner et al. |
| 2011/0269100 A1 | 11/2011 | Furrer et al. |
| 2011/0275032 A1 | 11/2011 | Tardieu et al. |
| 2011/0295887 A1 | 12/2011 | Palmese et al. |
| 2012/0010619 A1 | 1/2012 | Barsoum |
| 2012/0010710 A1 | 1/2012 | Frigg |
| 2012/0010711 A1 | 1/2012 | Antonyshyn et al. |
| 2012/0065640 A1 | 3/2012 | Metzger et al. |
| 2012/0078259 A1 | 3/2012 | Meridew |
| 2012/0089595 A1 | 4/2012 | Jaecksch |
| 2012/0101586 A1 | 4/2012 | Carson |
| 2012/0109137 A1 | 5/2012 | Iannotti et al. |
| 2012/0109138 A1 | 5/2012 | Meridew et al. |
| 2012/0109226 A1 | 5/2012 | Iannotti et al. |
| 2012/0130382 A1 | 5/2012 | Iannotti et al. |
| 2012/0136365 A1 | 5/2012 | Iannotti et al. |
| 2012/0141034 A1 | 6/2012 | Iannotti et al. |
| 2012/0143197 A1 | 6/2012 | Lang et al. |
| 2012/0143267 A1 | 6/2012 | Iannotti et al. |
| 2012/0209276 A1 | 8/2012 | Schuster |
| 2012/0215225 A1 | 8/2012 | Philippon et al. |
| 2012/0221017 A1 | 8/2012 | Bonutti |
| 2012/0226283 A1 | 9/2012 | Meridew et al. |
| 2012/0232596 A1 | 9/2012 | Ribeiro |
| 2012/0259335 A1 | 10/2012 | Scifert et al. |
| 2012/0265208 A1 | 10/2012 | Smith |
| 2012/0271314 A1 | 10/2012 | Stemniski et al. |
| 2012/0271366 A1 | 10/2012 | Katrana et al. |
| 2012/0277751 A1 | 11/2012 | Catanzarite et al. |
| 2012/0289965 A1 | 11/2012 | Gelaude et al. |
| 2012/0296339 A1 | 11/2012 | Iannotti et al. |
| 2012/0303004 A1 | 11/2012 | Uthgenannt et al. |
| 2012/0303033 A1 | 11/2012 | Weiner et al. |
| 2012/0310399 A1 | 12/2012 | Metzger |
| 2012/0316564 A1 | 12/2012 | Serbousek et al. |
| 2012/0323246 A1 | 12/2012 | Catanzarite et al. |
| 2013/0001121 A1 | 1/2013 | Metzger |
| 2013/0006250 A1 | 1/2013 | Metzger et al. |
| 2013/0035766 A1 | 2/2013 | Meridew |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| DE | 3447365 A1 | 7/1986 |
| DE | 04219939 A1 | 12/1993 |
| DE | 4421153 A1 | 12/1995 |
| DE | 102009028503 A1 | 2/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1634551 A2 | 3/2006 |
| EP | 1852072 A2 | 7/2007 |
| EP | 1832239 A1 | 9/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| FR | 2659226 A1 | 9/1991 |
| FR | 2721195 A1 | 12/1995 |

(56) References Cited

FOREIGN PATENT DOCUMENTS

| | | |
|---|---|---|
| FR | 2768916 A1 | 4/1999 |
| GB | 2094590 A | 9/1982 |
| GB | 2197790 A | 6/1988 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| JP | 59157715 A | 9/1984 |
| JP | 60231208 A | 11/1985 |
| JP | 2011505080 A | 2/2011 |
| JP | 2011527885 A | 11/2011 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| TW | 231755 | 5/2005 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-0226145 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051239 A1 | 6/2005 |
| WO | WO-2005051240 A1 | 6/2005 |
| WO | WO-2005077039 A2 | 8/2005 |
| WO | WO-2006058057 A2 | 6/2006 |
| WO | WO-2006060795 A1 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-2007041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096553 A1 | 8/2010 |
| WO | WO-2010096557 A2 | 8/2010 |
| WO | WO-2010124164 A1 | 10/2010 |
| WO | WO-2010144705 A1 | 12/2010 |
| WO | WO-2010148103 A1 | 12/2010 |
| WO | WO-2011018458 A1 | 2/2011 |
| WO | WO-2011041398 A1 | 4/2011 |
| WO | WO-2011060536 A1 | 5/2011 |
| WO | WO-2011019797 A3 | 7/2011 |
| WO | WO-2011106711 A1 | 9/2011 |
| WO | WO-2011109260 A1 | 9/2011 |
| WO | WO-2011110374 A1 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012061042 A1 | 5/2012 |
| WO | WO-2012058353 A4 | 6/2012 |
| WO | WO-2012058355 A4 | 7/2012 |
| WO | WO-2012058349 A4 | 8/2012 |
| WO | WO-2012116206 A1 | 8/2012 |
| WO | WO-2012158917 A1 | 11/2012 |
| WO | WO-2012173929 A1 | 12/2012 |
| WO | WO-2012174008 A1 | 12/2012 |

OTHER PUBLICATIONS

"Ascent Total Knee System," brochure. Biomet, Inc. (1999) 16 sheets.

"Customized Patient Instruments, Patient specific instruments for patient specific needs," brochure. (2008) DePuy Orthopaedics, Inc. 14 sheets.

"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.

"Discovery® Elbow System Surgical Technique," brochure. Biomet Orthopedics, Inc. (2008) pp. 1-25.

"Discovery® Elbow System," brochure. Biomet Orthopedics, Inc. (2007) 3 sheets.

"Hipsextant Instructions of Use." (2011) Surgical Planning Associates, Inc. 19 pages.

"Knee tensor combined with laser femoral head locator," Research Disclosure. Jul. 2006. No. 507; p. 903.

"Method for constructing an allograft sleeve." Research Disclosure (Dec. 2003) No. 476, p. 1294.

"OSS™ Orthopaedic Salvage System, Femoral/Tibial Augmentation," brochure. Biomet Orthopedics, Inc., (2003) pp. 1-8 (12 sheets).

"Patient Matched PMI Implants, C.A.M.R.A. 3-D Imaging," brochure, Biomet, Inc. (1990) 6 pages.

"Regenerex® Tibial Cone Augment, Surgical Technique Addendum to the Vanguard® SSK Revision System," brochure. Biomet® Orthopedics. (2009) pp. 1-8 (12 sheets).

"Signature™ Personalized Patient Care, Surgical Technique Addendum to the Vanguard Knee System" brochure. Biomet® Orthopedics, Inc. (2009) pp. 1-8.

"TruMatch™ Personalized knee replacement solutions," tri-fold brochure. (2009) SIGMA® DePuy Orthopaedics, Inc. 2 pages.

"Vanguard® PFR Partial Knee Patellofemoral Replacement System," Surgical Technique brochure. Biomet Orthopaedics, (2010) pp. 1-25.

"Zimmer® UniSpacer® Knee System," brochure. (2005) Zimmer, Inc. 4 sheets.

Birnbaum, Klaus, M.D., "Computer-Assisted Orthopedic Surgery With Individual Templates and Comparison to Conventional Method," Spine vol. 26, No. 4, pp. 365-370 (2001) Lippincott Williams & Wilkins, Inc.

Botha, Cheri P., Technical Report: DeVIDE—The Delft Visualisation and Image processing Development Environment, pp. 1-49 (May 31, 2006).

Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.

Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.

Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.

(56) References Cited

OTHER PUBLICATIONS

Haaker, R.G., et al., "Minimal-invasive navigiert implantierte unikondyläre Knieendoprothese," Orthopäde 2006 35:1073-1079 (2006) Spinger Medizin Verlag.

Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.

Hazen, Eric J., M.D., "Computer-Assisted Orthopaedic Sugery, A New Paradigm," Techniques in Orthopaedics® vol. 18, No. 2, (2003) pp. 221-229.

Hutmacher, Dietmar, W., "Scaffolds in tissue engineering bone and cartilage," Biomaterials, 2000 Elsevier Science Ltd. (pp. 2529-2543).

International Preliminary Report on Patentability and Written Opinion for PCT/US2009/039578 mailed Oct. 28, 2010 claiming benefit of U.S. Appl. No. 12/103,834, filed Apr. 16, 2008.

International Preliminary Report on Patentability and Written Opinion mailed Oct. 28, 2010 for PCT/US2009/039507 claiming benefit of U.S. Appl. No. 12/103,824, filed Apr. 16, 2008.

International Preliminary Report on Patentability for PCT/US2007/013223 mailed Dec. 24, 2008 claiming benefit of U.S. Appl. No. 11/756,057, filed May 31, 2007.

International Preliminary Report on Patentability mailed Mar. 31, 2011 for PCT/US2009/056670 claiming benefit of U.S. Appl. No. 12/211,407, filed Sep. 16, 2008.

International Search Report and Written Opinion for PCT/US2007/013223 mailed Nov. 26, 2007, claiming benefit of U.S. Appl. No. 11/756,057, filed May 31, 2007.

International Search Report and Written Opinion for PCT/US2009/039507 mailed Jul. 14, 2009, claiming benefit of U.S. Appl. No. 12/103,824.

International Search Report and Written Opinion for PCT/US2009/056670 mailed Mar. 2, 2010 claiming benefit of U.S. Appl. No. 12/211,407, filed Sep. 16, 2008.

International Search Report and Written Opinion mailed Apr. 22, 2010 for PCT/US2010/024579 claiming benefit of U.S. Appl. No. 12/389,930, filed Feb. 20, 2009.

International Search Report and Written Opinion mailed Aug. 19, 2010 for PCT/US2010/024584 claiming benefit of U.S. Appl. No. 12/389,901, filed Feb. 20, 2009.

International Search Report and Written Opinion mailed Dec. 7, 2010 for PCT/US2010/050701 claiming benefit of U.S. Appl. No. 12/571,969, filed Oct. 1, 2009.

International Search Report and Written Opinion mailed Jul. 31, 2009 for PCT/US2009/039578 claiming benefit of U.S. Appl. No. 12/103,834, filed Apr. 16, 2008.

International Search Report and Written Opinion mailed Jun. 10, 2010 for PCT/US2010/038177 claiming benefit of U.S. Appl. No. 12/483,807, filed Jun. 12, 2009.

International Search Report and Written Opinion mailed Jun. 4, 2010 for PCT/US2010/024073 filed Feb. 12, 2010, claiming benefit of U.S. Appl. No. 12/371,096, filed Feb. 13, 2009.

International Search Report and Written Opinion mailed May 9, 2011 for PCT/US2011/026412 claiming benefit of U.S. Appl. No. 12/872,663, filed Aug. 31, 2010.

International Search Report and Written Opinion mailed Oct. 5, 2010 for PCT/US2010/038845 claiming benefit of U.S. Appl. No. 12/486,992, filed Jun. 18, 2009.

Invitation to Pay Additional Fees mailed May 3, 2011 for PCT/US2011/026333 claiming benefit of U.S. Appl. No. 12/714,023, filed Feb. 26, 2010.

Invitation to Pay Additional Fees with Partial International Search mailed Nov. 26, 2009 for PCT/US2009/056670.

Kaus, Michael R., Ph.D., "Automated Segmentation of MR Images of Brain Tumors," Radiology, vol. 218, No. 2, (2001) pp. 586-591.

Kelly, Todd C., M.D., "Role of Navigation in Total Hip Arthroplasty." The Journal of Bone & Joint Surgery(2009) pp. 153-158. vol. 91-A, Supplement 1.

Klein, M., "Robot assisted insertion of craniofacial implants—clinical experience," CARS 2001, pp. 133-138 (2001) Elsevier Science B.V.

Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.

Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.

Murphy, S.B., et al. "The Hip Sextant: Navigation of Acetabular Component Orientation Using a Mechanical Instrument," brochure. (2009) 1 page.

Nicholls, Paul, M.D., "Trauma Grand Rounds PMI (Patient-Matched Implants)" brochure, Biomet Orthopedics, Inc., (Feb. 29, 2000) 1 page.

Overhoff, H.M., et al., "Total Knee Arthroplasty: Coordinate System Definition and Planning based on 3-D Ultrasound Image Volumes," CARS 2001, pp. 283-288, (2001) Elsevier Science B.V.

Portheine, F., "CT-basierte Planung und DISOS-Schablonennavigation in der Kniegelenkendoprothetik," in Navigation und Robotic in der Gelenk—und Wirbelsäulenchirugie, Kapitel 32, Springer Verlag (2003) pp. 262-269.

Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.

Portheine, K., "Development of a clinical demonstrator for computer assisted orthopedic surgery with CT-image based individual templates," Computer Assisted Radiology and Surgery, pp. 944-949, (1997) Elsevier Science B.V.

Radermacher, "Computer Assisted Orthopaedic Surgery with Image Based Individual Templates," Clinical Orthopaedics and Related Research No. 354, pp. 28-38 (1998) Lippincott Williams & Wilkins.

Radermacher, K., et al., "Computer Integrated Orthopaedic Surgery: Connection of Planning and Execution in Surgical Intervention," Computer-integrated surgery: technology and clinical applications, (1996) pp. 451-463.

Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.

Radermacher, K., et al., "Image Guided Orthopedic Surgery Using Individual Templates," Springer Berlin/Heidelberg, CVRMed-MRCAS'97, vol. 1205/1997 pp. 606-615).

Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.

Radermacher, Klaus, et al. "Computer Assisted Orthopaedic Individual Templates." Clinical Orthopaedics and Related Research. (Sep. 1998) No. 354; pp. 28-38.

Schuller-Götzburg, P., et al., 3D-Implantatplanung und Stereolithographie-Implantatbohrschablonen, Stomatologie 101.3, pp. 55-59 (2004).

Sharp, S. Michael, Ph.D., Patient-Specific, Resurfacing Bi-Compartmental Arthuroplasty, Futuretech, Orthopaedic Product News (Mar./Apr. 2008) pp. 12-15.

Sisto, Domenick, J., et al., "Custom Patellofemoral Arthroplasty of the Knee Surgical Technique," Journal of Bone and Joint Surgery, vol. 89-A, pp. 214-225 (2007).

Slammin, John et al, "Do You Have This Implant in My Size?", MDT Medical Design Technology, 3 pages, http://www.mdtmag.com/scripts/ShowPR.asp?PUBCODE=046&ACCT=0007796&Issue ... accessed Jul. 31, 2008.

Steinwachs, Matthias Reinhard, "Cartilage Repair—Autologous Chondrocyte Transplantation and Autologous Matrix-induced Chondrogenesis," European Musculoskeletal Review (2006) pp. 65-68.

Biomet "Oxford® Partial Knee" brochure, 8 pages (Feb. 2011).

(56) References Cited

OTHER PUBLICATIONS

Biomet "The Oxford® Partial Knee Surgical Technique," brochure, pp. 1-38, (Feb. 2010).
Biomet, "Oxford® Partial Knee Microplasty® Instrumentation Surgical Technique", brochure, pp. 1-54 (May 2011).
International Preliminary Report on Patentability and Written Opinion mailed Sep. 7, 2012 for PCT/US2011/026333 claiming benefit of U.S. Appl. No. 12/714,023, filed Feb. 26, 2010.
International Preliminary Report on Patentability for PCT/US2010/050701 mailed Apr. 12, 2012 claiming benefit of U.S. Appl. No. 12/571,969, filed Oct. 1, 2009.
International Search Report and Written Opinion mailed Mar. 5, 2012 for PCT/US2011/057300 claiming benefit of U.S. Appl. No. 12/938,905, filed Nov. 3, 2010.
International Search Report and Written Opinion mailed May 8, 2012 for PCT/US2012/026356 claiming benefit of U.S. Appl. No. 13/041,883, filed Mar. 7, 2011.
Thoma, W., et al., "Endoprothetischen Versorgung des Kniegelenks auf der Basis eines 3D-computertomographischen Subtraktionsversfahrens," Zuma Thema: Computergestützte orthopädische Chirugie, Der Orthopäde 29:641-644 Springer-Verlag (Jul. 2000) Translation provided: Thoma, W., "Endoprosthetic care of the knee joint based on a 3D computer chromatography subtraction process," Topic: Computer-aided orthopedic surgery. Orthopedist 2000 29:641-644 Springer Verlag (Jul. 2000).
"MAX-Ti™ Modular Protrusio Cage," Surgical Technique brochure. Biomet Orthopedics, Inc. (2003) 10 sheets.
"MAX-Ti™ Modular Protrusio Cage," Surgical Technique brochure. Biomet Orthopedics, Inc. (2006) 12 sheets.
"PAR 5™ Protrusio Acetabular Reconstruction System," brochure. (2006) Biomet Orthopedics, Inc. 12 sheets.
International Preliminary Report on Patentability mailed Aug. 25, 2011 for PCT/US2010/024073 filed Feb. 12, 2010, claiming benefit of U.S. Appl. No. 12/371,096, filed Feb. 13, 2009.
International Preliminary Report on Patentability mailed Sep. 1, 2011 for PCT/US2010/024579 claiming benefit of U.S. Appl. No. 12/389,930, filed Feb. 20, 2009.
International Preliminary Report on Patentability mailed Sep. 1, 2011 for PCT/US2010/024584 claiming benefit of U.S. Appl. No. 12/389,901, filed Feb. 20, 2009.
International Search Report and Written Opinion mailed Aug. 9, 2011 for PCT/US2011/026333 claiming benefit of U.S. Appl. No. 12/714,023, filed Feb. 26, 2010.
Great Britain Search Report mailed Dec. 21, 2011 for GB1116054.6, claiming benefit of U.S. Appl. No. 12/888,005, filed Sep. 22, 2010.
International Preliminary Report and Written Opinion mailed Jan. 5, 2012 for PCT/US2010/038845 claiming benefit of U.S. Appl. No. 12/486,992, filed Jun. 18, 2009.
International Preliminary Report on Patentability and Written Opinion mailed Dec. 22, 2011 for PCT/US2010/038177 claiming benefit of U.S. Appl. No. 12/483,807, filed Jun. 12, 2009.
International Search Report mailed Nov. 30, 2010 for PCT/EP2010/061630 filed Aug. 10, 2010 claiming benefit of DE102009028503.2 filed Aug. 13, 2009.
Supplementary European Search Report mailed Nov. 15, 2011 for EP07809326, which claims benefit of PCT/US2007/013223, filed Jun. 5, 2007; which claims priority to U.S. Appl. No. 11/756,057, filed May 31, 2007.
"Comprehensive® Reverse Shoulder System Surgical Technique," Biomet Orthopedics brochure (2009-2012), 48 pages.
"Comprehensive® Reverse Shoulder System Technical Design Features," Biomet Orthopedics brochure (2009), 3 pages.
"Comprehensive® Reverse Shoulder System," Biomet Orthopedics brochure (2009), 8 pages.
"Comprehensives® Shoulder System Surgical Technique," Biomet Orthopedics brochure (2007), pp. 1-53.
"Comprehensive® Total Shoulder System," Biomet Orthopedics brochure (2011), 4 pages.
Friedman, R.J. et al., "The Use of Computerized Tomography in the Measurement of Glenoid Version", Journal of Bone & Joint Surgery Am. (JBJS) 1992;74:1032-1037 (Aug. 1992).
International Search Report and Written Opinion mailed Dec. 18, 2012 for PCT/US2012/059189, which claims benefit of U.S. Appl. No. 13/597,478, filed Aug. 29, 2011.
International Search Report and Written Opinion mailed Feb. 6, 2013 for PCT/US2012/060842, which claims benefit of U.S. Appl. No. 13/653,868, filed Oct. 17, 2012.
International Search Report and Written Opinion mailed Feb. 6, 2013 for PCT/US2012/060854, which claims benefit of U.S. Appl. No. 13/653,893, filed Oct. 17, 2012.
International Search Report and Written Opinion mailed Nov. 15, 2012, for PCT/US2012/052853, which claims benefit of U.S. Appl. No. 13/221,968, filed Aug. 31, 2011.
International Search Report mailed Oct. 23, 2012, for PCT/US2012/041893, which claims benefit of U.S. Appl. No. 61/496,177, filed Jun. 13, 2011.
Invitation to Pay Additional Fees mailed Feb. 6, 2013 for PCT/US2012/060848, which claims benefit of U.S. Appl. No. 13/653,878, filed Oct. 17, 2012.
Invitation to Pay Additional Fees mailed Feb. 7, 2013 for PCT/US2012/060853, which claims benefit of U.S. Appl. No. 13/653,893, filed Oct. 17, 2012.
International Search Report and Written Opinion for PCT/US2013/026875 mailed Jun. 7, 2013, claiming benefit of U.S. Appl. No. 13/400,652, filed Feb. 21, 2012.
International Preliminary Report on Patentability mailed Sep. 6, 2013 for PCT/US2012/026356 claiming benefit of U.S. Appl. No. 13/041,883, filed Mar. 7, 2011.
International Search Report and Written Opinion mailed Oct. 14, 2013 for PCT/US2013/057097 claiming benefit of U.S. Appl. No. 13/597,478, filed Aug. 29, 2012.

\* cited by examiner

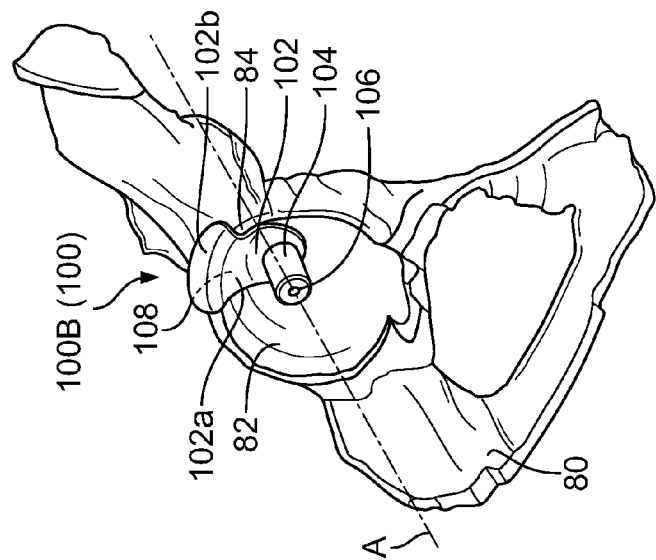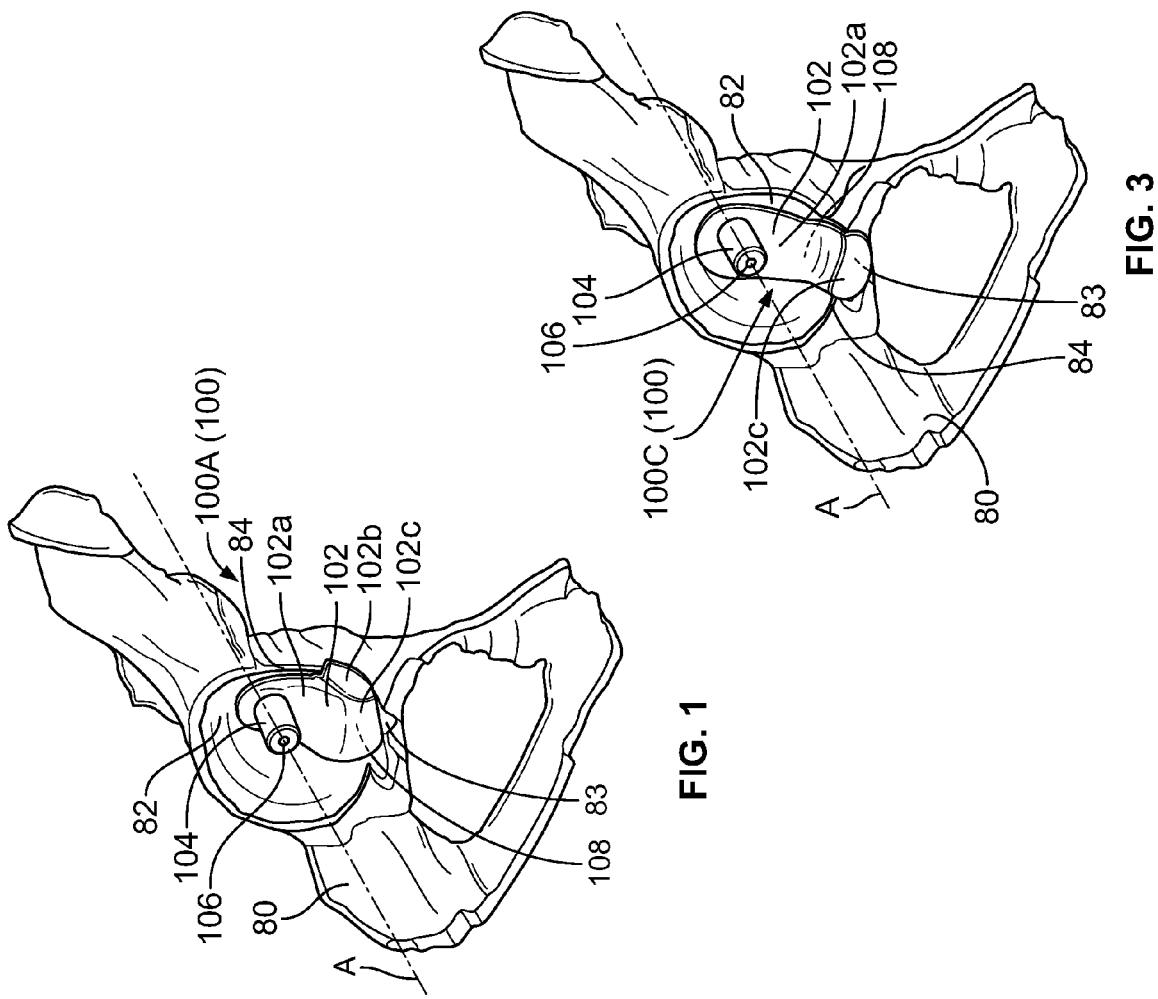

PATIENT-SPECIFIC ACETABULAR GUIDES AND ASSOCIATED INSTRUMENTS

CROSS-REFERENCE TO RELATED APPLICATIONS

This application claims the benefit of U.S. Provisional Application No. 61/446,660, filed on Feb. 25, 2011.

This application is a continuation-in-part of U.S. application Ser. No 12/978,069 filed Dec. 23, 2010, which is a continuation-in-part of U.S. application Ser. No. 12/973,214, filed Dec. 20, 2010, which is a continuation-in-part of U.S. application Ser. No. 12/955,361 filed Nov. 29, 2010, which is a continuation-in-part of U.S. application Ser. Nos. 12/938,905 and 12/938,913, both filed Nov. 3, 2010, each of which is a continuation-in-part of U.S. application Ser. No. 12/893,306, filed Sep. 29, 2010, which is continuation-in-part of U.S. application Ser. No. 12/888,005, filed Sep. 22, 2010, which is a continuation-in-part of U.S. application Ser. No. 12/714,023, filed Feb. 26, 2010, which is a continuation-in-part of U.S. application Ser. No. 12/571,969, filed Oct. 1, 2009, which is a continuation-in-part of U.S. application Ser. No. 12/486,992, filed Jun. 18, 2009, and is a continuation-in-part of U.S. application Ser. No. 12/389,901, filed Feb. 20, 2009, which is a continuation-in-part of U.S. application Ser. No. 12/211,407, filed Sep. 16, 2008, which is a continuation-in-part of U.S. application Ser. No. 12/039,849, filed Feb. 29, 2008, which: (1) claims the benefit of U.S. Provisional Application No. 60/953,620, filed on Aug. 2, 2007, U.S. Provisional Application No. 60/947,813, filed on Jul. 3, 2007, U.S. Provisional Application No. 60/911,297, filed on Apr. 12, 2007, and U.S. Provisional Application No. 60/892,349, filed on Mar. 1, 2007; (2) is a continuation-in-part U.S. application Ser. No. 11/756,057, filed on May 31, 2007, which claims the benefit of U.S. Provisional Application No. 60/812,694, filed on Jun. 9, 2006; (3) is a continuation-in-part of U.S. application Ser. No. 11/971,390, filed on Jan. 9, 2008, which is a continuation-in-part of U.S. application Ser. No. 11/363,548, filed on Feb. 27, 2006; and (4) is a continuation-in-part of U.S. application Ser. No. 12/025,414, filed on Feb. 4, 2008, which claims the benefit of U.S. Provisional Application No. 60/953,637, filed on Aug. 2, 2007.

This application is continuation-in-part of U.S. application Ser. No. 12/872,663, filed on Aug. 31, 2010, which claims the benefit of U.S. Provisional Application No. 61/310,752 filed on Mar. 5, 2010.

This application is a continuation-in-part of U.S. application Ser. No. 12/483,807, filed on Jun. 12, 2009, which is a continuation-in-part of U.S. application Ser. No. 12/371,096, filed on Feb. 13, 2009, which is a continuation-in-part of U.S. application Ser. No. 12/103,824, filed on Apr. 16, 2008, which claims the benefit of U.S. Provisional Application No. 60/912,178, filed on Apr. 17, 2007.

This application is also a continuation-in-part of U.S. application Ser. No. 12/103,834, filed on Apr. 16, 2008, which claims the benefit of U.S. Provisional Application No. 60/912,178, filed on Apr. 17, 2007.

The disclosures of the above applications are incorporated herein by reference.

INTRODUCTION

The present teachings provide various instruments and methods for preparing a joint surface, such as an acetabulum, for example, to receive an implant and guiding the implant along a patient-specific alignment axis.

SUMMARY

The present teachings provide various instruments and methods for generally preparing a joint-surface of a patient to receive an implant along a patient-specific alignment axis. The instruments and methods are illustrated for the acetabulum of the hip joint. The alignment axis and various patient-specific guides and instruments can be designed during a pre-operative plan using a three-dimensional reconstruction of the patient's relevant anatomy, such as the pelvis or portions thereof, including the acetabular and periacetabular areas of the pelvis. The three-dimensional reconstruction can be based on two-dimensional medical images, including MRI, CT or X-ray scans and prepared using commercially available imaging software.

In some embodiments, the present teachings provide a method for preparing a joint surface of a patient for an implant, such as, for example, an acetabular implant for a hip joint. According to the method, a patient-specific guide is attached to a complementary joint surface of the patient. The patient-specific guide includes a guiding element oriented along a patient-specific alignment axis. The alignment axis is determined during a preoperative plan of the patient for implant alignment. A shaft of a guiding tool is removably coupled to the guiding element of the guide. A three-dimensional orientation device is removably attached and can be keyed to the shaft of the guiding tool. A position of a bubble of the orientation device is marked with a mark on an outer transparent surface of the orientation device while the guiding tool is oriented along the alignment axis. In some embodiments, the guiding tool can be an acetabular inserter fitted with a removable adapter tip.

The orientation device, as marked, can be used for aligning other instruments during the procedure. For example, the orientation device can be used with a shaft of a reamer to align the reamer along the alignment axis. The orientation device can also be used with a shaft of an acetabular inserter of an implant for inserting and implanting the implant into the joint. A number of orientation devices can be provided in a surgical kit including one or more patient-specific guides, modular handles, tools and shafts, reamer or other cutting tools, inserters or implant impactors. The surgical kit can also include one or more implant components. The orientation devices can be reusable or disposable.

The acetabular guide can be provided in various fitment options in which the patient-specific engagement surface includes additional portions complementary to a portion of the acetabular rim and/or a portion of the transverse acetabular ligament.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIGS. 1-5 illustrate environmental perspective views of various patient-specific acetabular alignment guides according to the present teachings;

DESCRIPTION OF VARIOUS ASPECTS

Figure 4:
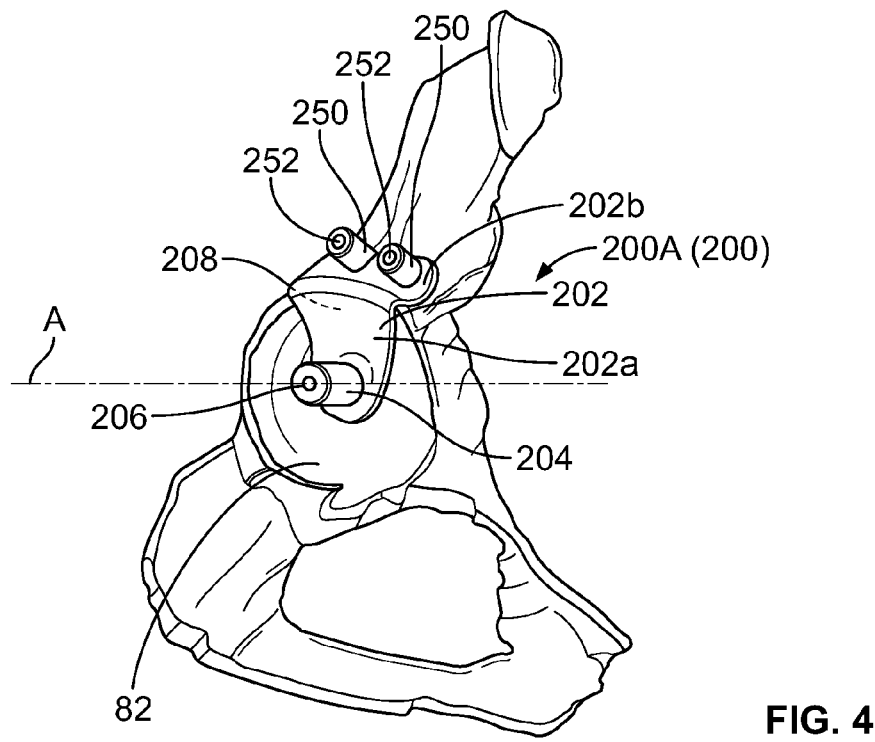

The following description is merely exemplary in nature and is in no way intended to limit the present teachings, applications, or uses.

The present teachings generally provide various patient-specific acetabular alignment guides, secondary guides, reamers, inserters, impactors and other associated instruments for use in orthopedic surgery, such as in joint replacement or revision surgery, for example. The patient-specific alignment guides and associated instruments can be used either with conventional or with patient-specific implant components prepared with computer-assisted image methods.

As described in commonly assigned U.S. application Ser. No. 11/756,057, filed on May 31, 2007, during a preoperative planning stage, imaging data of the relevant anatomy of a patient can be obtained at a medical facility or doctor's office. The imaging data can include, for example, a detailed scan of a pelvis, hip, knee, ankle or other joint or relevant portion of the patient's anatomy. The imaging data can be obtained using an MRI, CT, X-Ray, ultrasound or any other imaging system. The imaging data obtained can be used to construct a three-dimensional computer image of the joint or other portion of the anatomy of the patient and prepare an initial pre-operative plan that can include bone or joint preparation, including planning for resections, milling, reaming, broaching, implant selection and fitting, design of patient-specific guides, templates, tools and alignment protocols for the surgical procedure.

Computer modeling for obtaining three-dimensional computer images of the relevant patient's anatomy can be provided by various CAD programs and/or software available from various vendors or developers, such as, for example, from Materialise USA, Plymouth, Mich. The computer modeling program can be configured and used to plan a preoperative surgical plan, including planning various bone preparation procedures, to select or design/modify implants and design patient-specific guides and tools. The patient-specific components include patient-specific implants, and patient-specific tools, including reaming, broaching, milling, drilling or cutting tools, alignment guides, templates and other patient-specific instruments.

The pre-operative plan can be stored in any computer storage medium, in a computer file form or any other computer or digital representation. The pre-operative plan, in a digital form associated with interactive software, can be made available via a hard medium, a web-based or mobile or cloud service, or a cellular portable device to the surgeon or other medical practitioner, for review. Using the interactive software, the surgeon can review the plan, and manipulate the position of images of various implant components relative to an image of the anatomy. The surgeon can modify the plan and send it to the manufacturer with recommendations or changes. The interactive review process can be repeated until a final, approved plan, is sent to a manufacturing facility for preparing the actual physical components.

After the surgical plan is approved by the surgeon, patient-specific implants and associated tools, including, for example, alignment guides, cutting/milling/reaming/broaching or other tools for the surgical preparation of the joint or other anatomy portion of the specific patient can be designed using a CAD program or other three-dimensional modeling software, such as the software provided by Materialise, for example, according to the preoperative surgical plan. Patient-specific guides and other instruments can be manufactured by various stereolithography methods, selective laser sintering, fused deposition modeling or other rapid prototyping methods. In some embodiments, computer instructions of tool paths for machining the patient-specific guides and/or implants can be generated and stored in a tool path data file. The tool path data can be provided as input to a CNC mill or other automated machining system, and the tools and implants can be machined from polymer, ceramic, metal or other suitable material depending on the use, and sterilized. The sterilized tools and implants can be shipped to the surgeon or medical facility for use during the surgical procedure.

Patient-specific implants, guides, templates, tools or portions thereof are defined herein as those constructed by a surgical plan approved by the surgeon using thee-dimensional images of the specific patient's anatomy and made to closely conform and mate substantially as a negative mold of corresponding portions of the patient's anatomy, including bone surfaces with or without associated soft tissue, such as articular cartilage, for example, depending on the particular procedure, implant and tool use.

Patient-specific alignment guides and implants are generally configured to match the anatomy of a specific patient. The patient-specific alignment guides are generally formed using computer modeling based on the patient's 3-D anatomic image and have an engagement surface that is made to conformingly contact and match a three-dimensional image/ model of the patient's bone surface (with or without cartilage or other soft tissue), by the computer methods discussed above. The patient-specific alignment guides can include custom-made guiding formations, such as, for example, guiding bores or cannulated guiding posts or cannulated guiding extensions or receptacles that can be used for supporting or guiding other instruments, such as drill guides, reamers, cutters, cutting guides and cutting blocks or for inserting pins or other fasteners according to a surgeon-approved pre-operative plan. The patient-specific alignment guides can be used in minimally invasive surgery, and also in surgery with multiple minimally-invasive incisions. Various alignment guides and pre-operative planning procedures are disclosed in commonly assigned and co-pending U.S. patent application Ser. No. 11/756,057, filed on May 31, 2007; U.S. patent application Ser. No. 12/211,407, filed Sep. 16, 2008; U.S. patent application Ser. No. 11/971,390, filed on Jan. 9, 2008, U.S. patent application Ser. No. 11/363,548, filed on Feb. 27, 2006; and U.S. patent application Ser. No. 12/025,414, filed Feb. 4, 2008. The disclosures of the above applications are incorporated herein by reference.

Referring to FIGS. 1-5, the present teachings provide various patient-specific acetabular guides 100, 200. The acetabular guides 100, 200 can be used in connection with various other instruments to facilitate guided reaming of an acetabulum 82 of a pelvis 80 of a specific patient and guided insertion and implantation of an acetabular implant or acetabular cup in the acetabulum 82. Further, the patient-specific acetabular guides 100, 200 engage the acetabulum 82 of the specific patient in a unique (only one) position and can provide an accurate alignment axis relative to the planned orientation of the acetabular cup 280 (shown in FIG. 9, for example). The patient-specific acetabular guides 100, 200 can also provide secure fitting and rotational stability in a design that is lightweight with minimal size and bulk.

FIGS. 1-3 illustrate a patient-specific acetabular guide 100 having a patient-specific body 102, as described below, and a guiding or pilot element 104 having an elongated bore 106 with a patient-specific alignment axis A. The alignment axis A is configured to be central to the acetabular cup and perpendicular to the acetabular cup's surface when the acetabular guide 100 is positioned on the acetabulum 82. The acetabular guide 100 can be provided in various fitment options depending on the planned exposure of the acetabulum 82 for the reaming procedure and implantation. Each fitment option of the acetabular guide 100 can include a portion that covers the acetabular fossa at the center of the acetabulum 82, which provides a landmark for rotational stability and unique positioning on the acetabulum. Each fitment option can include additional portions complementary to a portion of the acetabular rim 84 and/or a portion of the transverse acetabular ligament 83, as discussed below in further detail. Each fitment option allows the acetabular guide 100 to have a compact size, extend through the center of the acetabulum 82 for alignment, and include portions that can fit over various anatomic landmarks in a unique position for the patient. The particular fitment option can be selected for each specific patient based on the patient's anatomy, the procedure to be performed and the surgeon's preference and/or technique.

Three exemplary fitment options designated 100A, 100B and 100C are illustrated in FIGS. 1-3, respectively. The fitment options can include fitments engaging or registering to various combinations of portions of the acetabulum 82, the acetabular rim 84 and the transverse acetabular ligament 83. For example, the acetabular guide 100 in the fitment option 100A may engage portions of the acetabulum 82, the acetabular rim 84 and the transverse acetabular ligament 83. In the fitment option 100B, the acetabular guide 100 may engage portions of the acetabulum 82 and the acetabular rim 84. In the fitment option 100C, the acetabular guide 100 may engage portions of the acetabulum 82 and the transverse acetabular ligament 83. Either one or several acetabular guides (or fitment options) 100A, 100B, 100C corresponding to different fitment options can be provided to the surgeon for intra-operative flexibility and plan change, according to the surgeon's preference. The acetabular guide 100 can be secured to the patient's bone with bone pins, guide wires or other fasteners.

The patient-specific body 102 of the acetabular guide 100 can include an inner portion 102a (all fitment options) from which the guiding element extends and which is designed to engage the acetabulum 82, an outer portion 102b which extends from the inner portion 102a and is configured to extend over a portion of the rim 84 (for fitment options 100A and 100C) and an outer portion 102c (fitment options 100A and 100C) configured to extend over a portion of the transverse acetabular ligament 83 (and adjacent area of the acetabulum 82). The patient specific body 102 has an underside three-dimensional engagement surface 108 that is custom-made or patient-specific to conform to and mirror complementary surfaces of various combinations of the acetabulum 82, rim 84 and/or transverse acetabular ligament 83 or other periacetabular surfaces of the pelvis 80 of the specific patient, as described above in connection with the various fitment options. The patient specific body 102 is designed by using a three-dimensional image or model of the acetabulum 82 and surrounding pelvic area of the patient, as described above. The engagement surface 108 enables the acetabular guide 100 to nest or closely mate relative to the complementarily acetabular surface of the patient. The acetabular guide 100 can be designed to have generally small thickness, such that it can form a lightweight three-dimensional shell from which the guiding element 104 extends opposite to the engagement surface. The guiding element 104 can be formed to be a monolithic or integral portion of the acetabular guide 100. Alternatively, the guiding element 104 can be modularly and removably coupled to the acetabular guide 100, using, for example, a threaded connection, snap-on connectors or other removable attachments.

Figure 5:
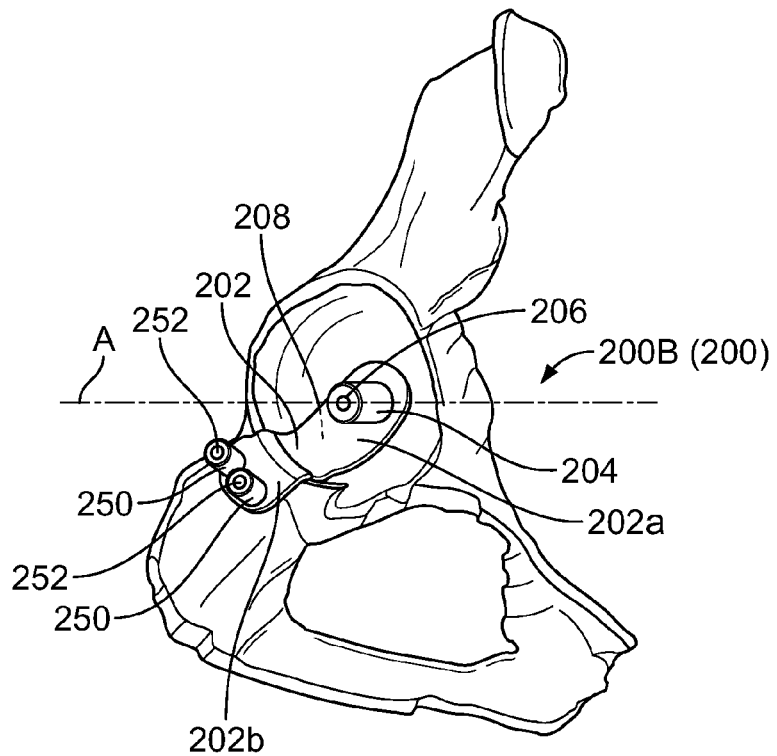
Figure 12:
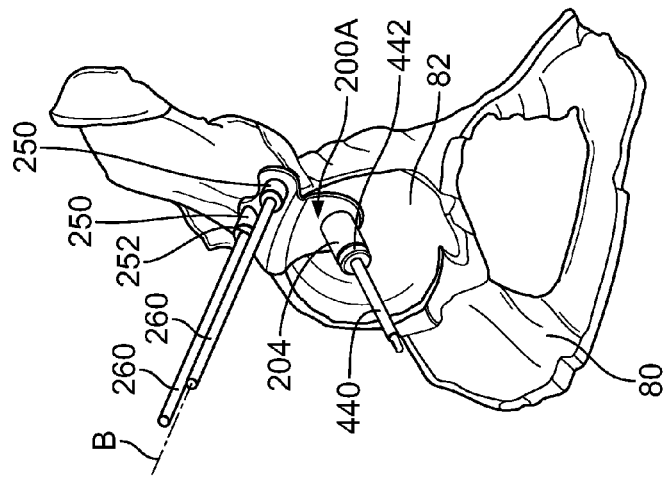
FIG. 12 is an environmental perspective view of the patient-specific acetabular alignment guide of FIG. 10 illustrating drilling a pilot hole for guided reaming according to the present teachings.
Figure 10:
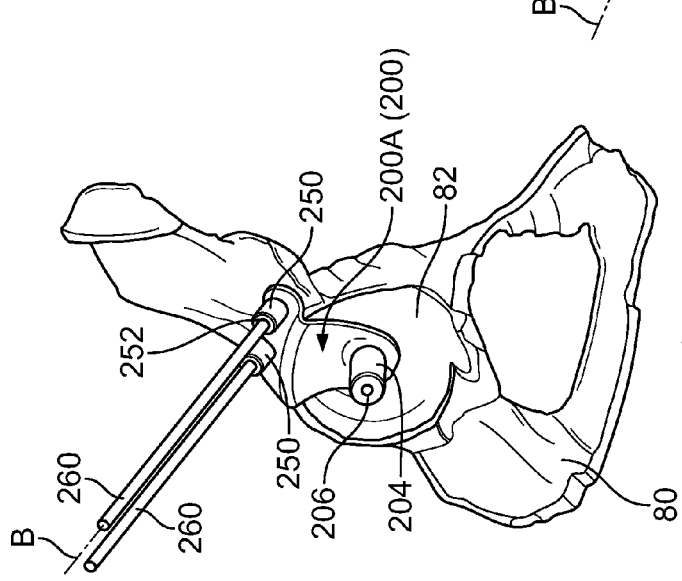
FIG. 10 is an environmental perspective view of a patient-specific acetabular alignment guide with alignment pins for a secondary guide according to the present teachings.
Figure 13:
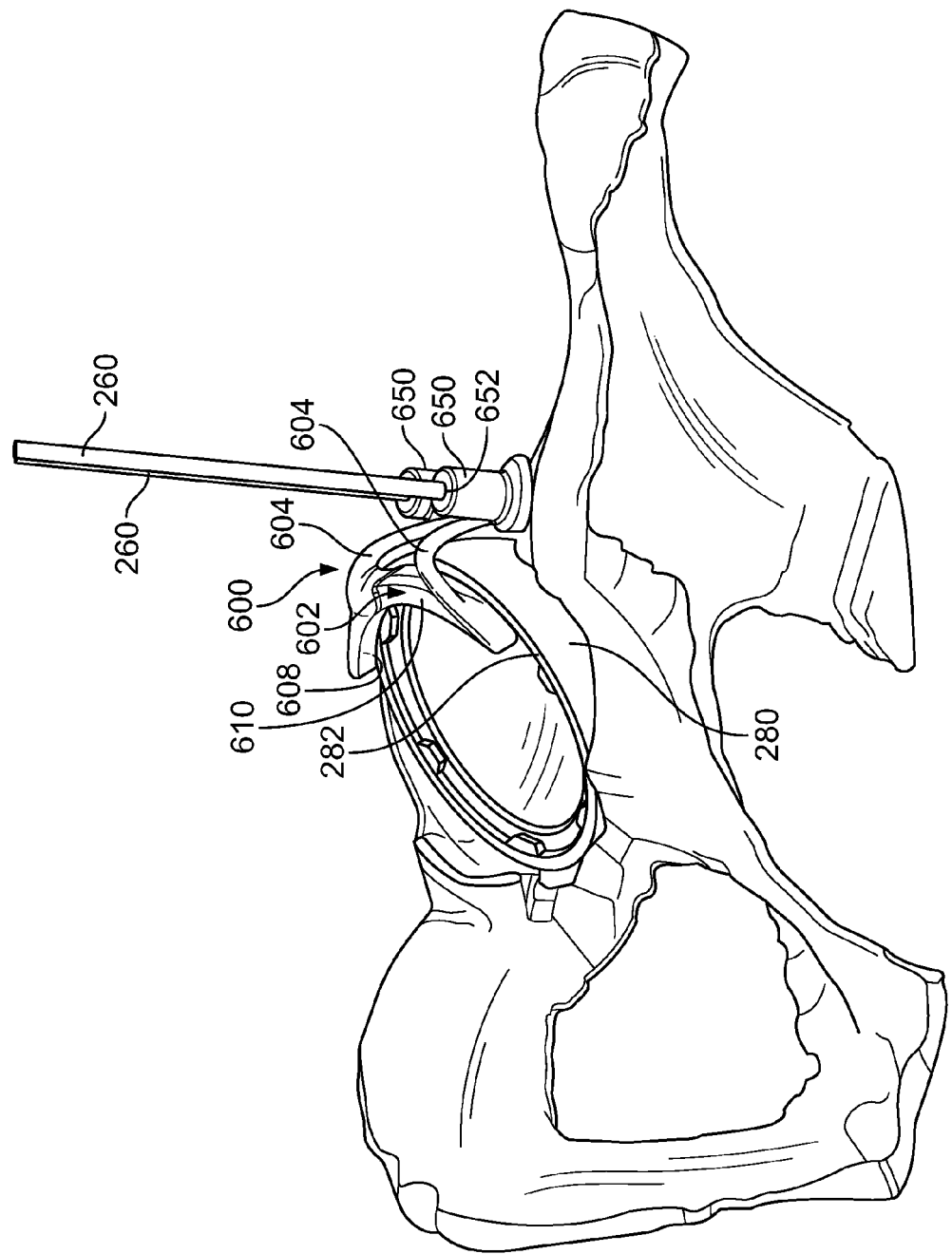
FIG. 13 is an environmental perspective view of a secondary guide over the alignment pins of FIG. 10 according to the present teachings.

Referring to FIGS. 4 and 5, another patient-specific acetabular guide 200 is illustrated with two exemplary fitment options 200A and 200B. Similarly to the acetabular guide 100, the acetabular guide 200 also includes a patient-specific body 202 and a guiding or pilot element 204 having an elongated bore 206 with an alignment axis A configured to be central to the acetabular cup and perpendicular to the acetabular cup's surface when the acetabular guide 200 is positioned on the acetabulum 82. The acetabular guide 200 can include one or more marker elements 250 (two are shown in the exemplary embodiments of FIGS. 4 and 5), each having an elongated bore 252 for guiding marker pins 260. The marker pins 260 can be used for supporting a secondary guide for another preparation method discussed below in reference to FIG. 12. The other features of the acetabular guide 200 are similar to that of the acetabular guide 100, such that the acetabular guide 200 can also be used instead of the acetabular guide 100. The acetabular guide 100 can be used for procedures in which the marker elements 250 are not utilized, as described below. The acetabular guide 200 can be used for procedures in which the marker elements 250 may or may not be utilized, as described below.

The patient-specific body 202 of the acetabular guide 200 is generally similar to patient-specific body 102 of the acetabular guide 100, such that the patient-specific body 202 can include an inner portion 202a from which the guiding element extends and which is designed to engage the acetabulum 82, and an outer portion 202b which extends from the inner portion 202a and is configured to extend over a rim portion 84 of the acetabulum 82. The outer portion 202b extends sufficiently beyond the rim 84 to the periacetabular area of the pelvis to accommodate the marker elements 250. The patient specific body 202 has an underside bone-engaging three-dimensional engagement surface 208 that is custom-made or patient-specific to conform and mirror in complementary surfaces of the acetabulum 82, rim 84 (with or without the transverse acetabular ligament 83) or other periacetabular surfaces of the pelvis 80 of the specific patient by using a three-dimensional image or model of the acetabulum and surrounding pelvic area of the patient, as described above. The engagement surface 208 enables the acetabular guide 100 to nest or closely mate relative to the complementarily acetabular surface of the patient. The acetabular guide 200 can be designed to have generally small thickness, such that it can form a lightweight three-dimensional shell from which the guiding element 204 and marker elements 250 extend.

Figure 6:
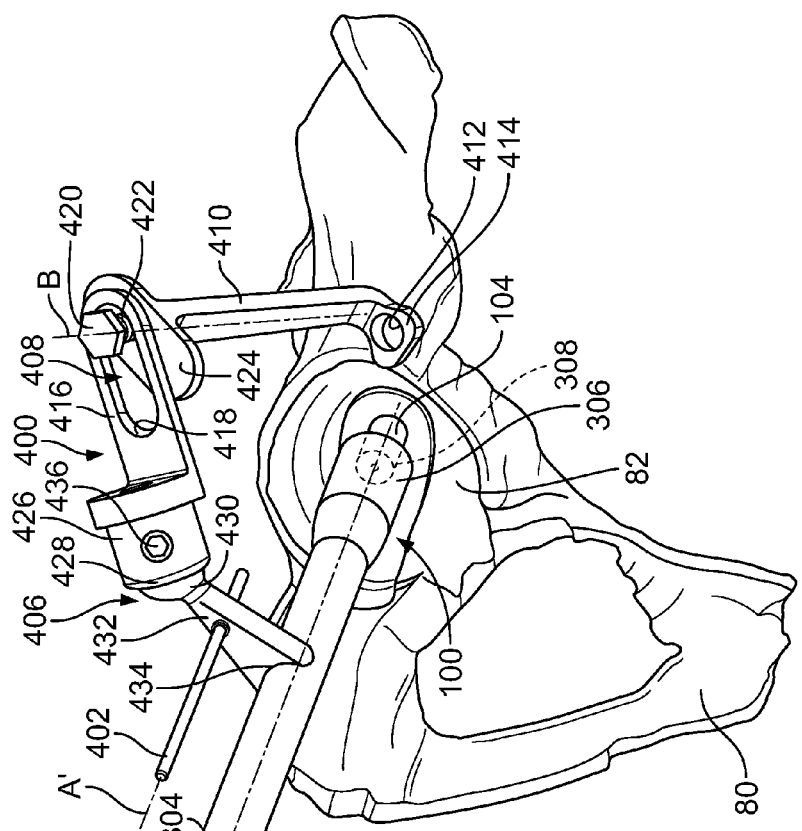
FIG. 6 is an environmental perspective view of various instruments illustrating a method for establishing an acetabular cup insertion axis according to the present teachings.

Referring to FIGS. 6-9, a method for reaming and preparing the acetabulum for an implant is described in connection with the patient-specific acetabular guides 100. The acetabular guides 200 can also be used, although the marker elements 250 are not utilized in this method. Referring to FIG. 6, a patient-specific acetabular guide 100 (or 200) is placed in a unique position on the acetabulum/rim/transverse acetabular ligament depending on the fitment option, as determined in the preoperative plan for the specific patient, and establishes the alignment axis A along the guiding element 104. An elongated guiding tool 300, such as a guiding handle 300 can be attached to the guiding element 104 such that the center axis of the guiding handle 300 coincides with the alignment axis A. The guiding handle 300 can include a proximal gripping portion 302, an elongated shaft 304 extending from the gripping portion 302 and a coupling distal portion or removable adapter tip 306 which can be removably coupled to the guiding element 104 such that the guiding handle 300 is aligned along the alignment axis A. The distal portion 306 can include, for example, a bore 308 for receiving the guiding element 104. The guiding element 104 and the bore 308 can be of sufficient length for the guiding handle 300 to be removably yet stably coupled to the guiding element 104 for indicating the alignment axis A without wobbling or other misaligning motion. The guiding tool 300 can also be an acetabular cup inserter, such as the inserter 550 illustrated in FIGS. 9 and 16, which can be fitted with the removable adapter tip 306 for removably connecting to the guiding element 104.

With continuing reference to FIG. 6, a support device or jig or outrigger 400 can be secured on the pelvis 80. The support device 400 can be used to orient an alignment pin or rod 402 along an axis A' parallel to the alignment axis A. More specifically, the support device 400 can include a universal rotational adjustment mechanism 406 and a pivotable/translational adjustment mechanism 408 for removably engaging the shaft 304 and aligning the alignment rod 402 parallel to the shaft 304 and, therefore, parallel to the alignment axis. In the exemplary embodiment of FIG. 6, the support device 400 can include a leg 410 that can be attached to the bone with a bone fastener through a hole 412 at a foot or base 414 of the leg 410. The support device 400 can also include an arm 416 that is slidably coupled to the leg 410 to allow for translational motion of the arm 416 relative to the leg 410. The arm 416 can have, for example, an elongated slot 418 that slidably receives a fastener head 420 of a fastener 422, such as a screw or bolt that is received through a distal flange 424 of the leg 410. The flange 424 can also pivot relative to the arm 416 about an axis B along the axis of the leg 410 and fastener 422. The head 420 of the fastener 422 can be rotated to lock the flange 424 and the leg 410 relative to the arm 416. The interconnection of the arm 416, the leg 410 and the fastener 422 collectively form the pivotable/translational adjustment mechanism 408.

With continued reference to FIG. 6, the arm 416 can be substantially planar and include at a distal end a housing 426 forming a socket 428 for a ball 430 at a distal end of a connector 432. The socket 428 and the ball 430 form a universal (ball) joint of the universal rotational adjustment mechanism 406 for rotationally adjusting the connector 432 relative to the arm 416. After adjustment, the orientation of the connector 432 can be locked with a fastener 436 through the housing 426. The connector 432 supports the alignment rod 402 and includes an engagement surface 434 that can engage the shaft 304, by a snap-on or other quick connect/disconnect connection. The support device 400 can be adjusted using the adjustment mechanisms 406, 408 described above such that the alignment rod 402 along axis A' is parallel to the alignment axis A of the shaft 304. In other words, the alignment rod 402 can serve as a marker for the orientation of the alignment axis A to guide reaming and cup insertion procedures as discussed below.

Figure 7:
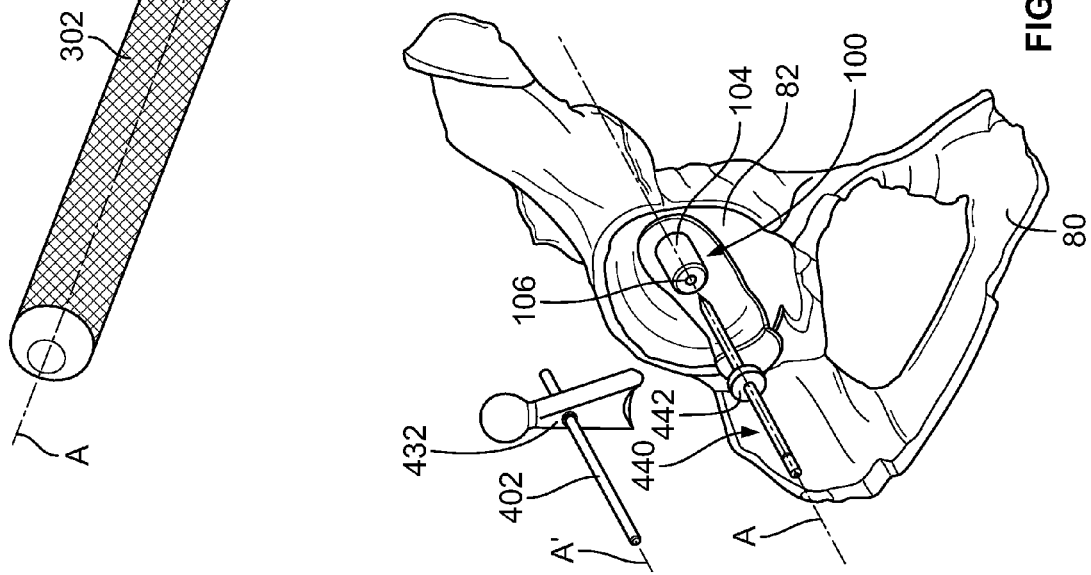
FIG. 7 is an environmental perspective view illustrating drilling a pilot hole for guided reaming according to the present teachings.
Figure 8A:
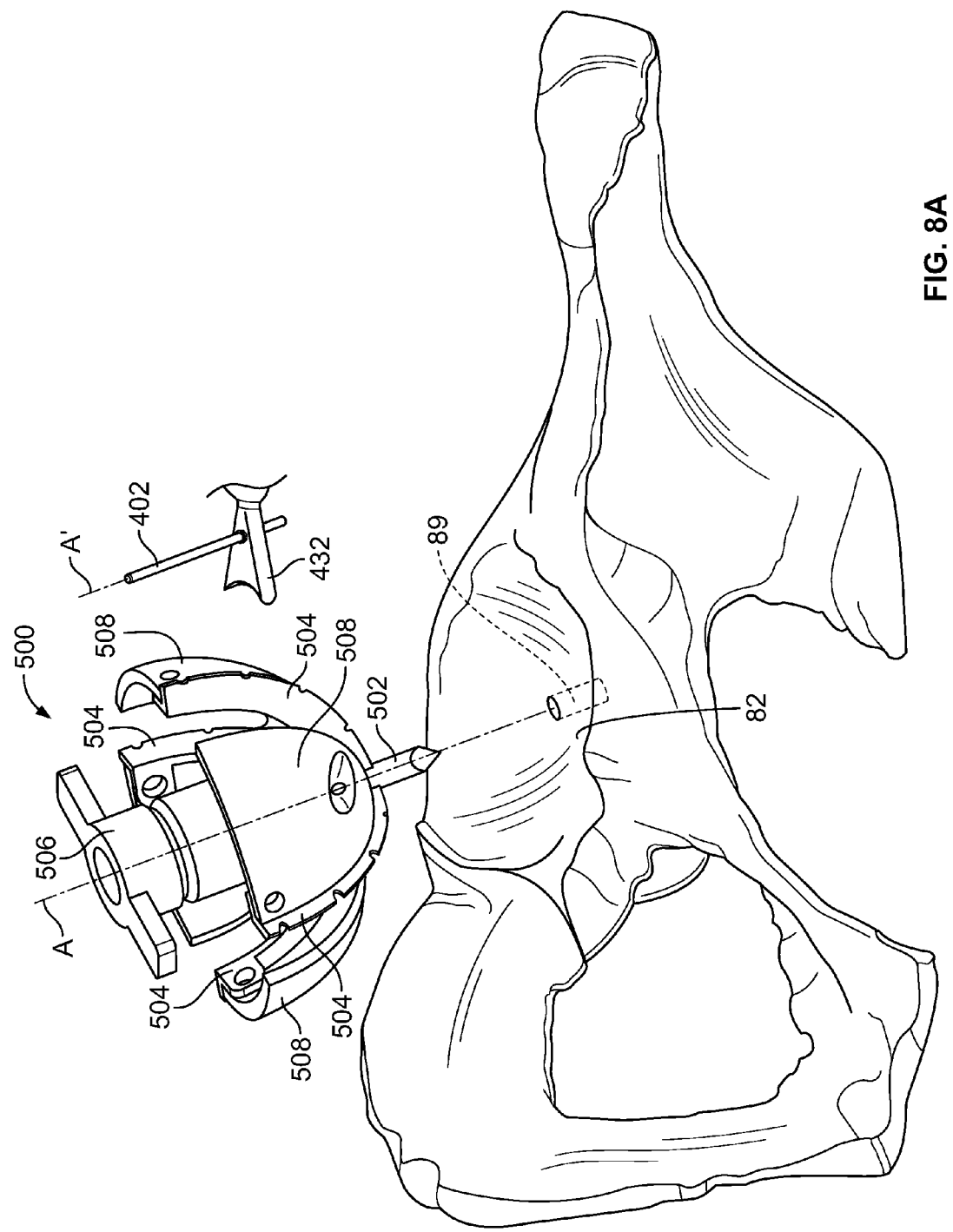
FIG. 8A is an environmental perspective view illustrating a reamer for guided reaming according to the present teachings.

After the support device 400 is locked in a position such that the orientation of the alignment rod 402 along axis A' is fixed and parallel to the alignment axis A, the guiding handle 300 (or the acetabular inserter 550) is disengaged from the engagement surface 434 of the connector 432 and the acetabular guide 100 and is removed. Referring to FIG. 7, a drilling element 440 can be guided through the bore 106 of the guiding element 104 of the acetabular guide 100 to drill a pilot hole 89 in the acetabulum 82 along the alignment axis A, as shown in FIG. 8A. The drilling element 440 can include a stop 442 at a pre-determined position to prevent over drilling or drilling through the wall of the acetabulum 82. The depth of drilling and the location of the stop 442 on the drilling element 440 can be determined during the pre-operative plan for the specific patient. The support device 400 and alignment rod 402 remain attached to the pelvis as shown in FIG. 6, although not fully shown in FIG. 7. After the pilot hole 89 is drilled, the acetabular guide 100 is removed.

Figure 8C:
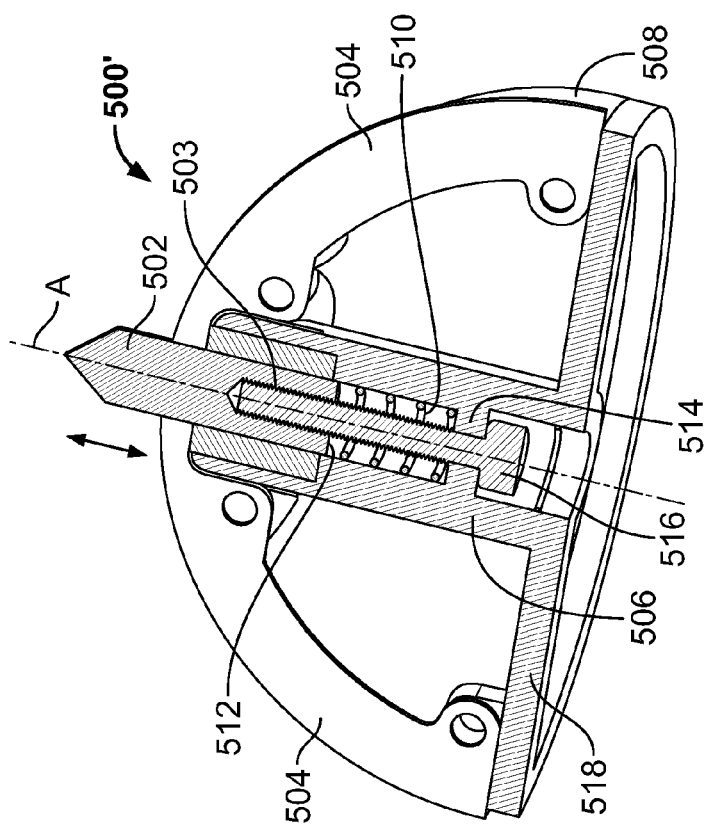
FIG. 8C is a partially sectioned perspective view of the reamer of FIG. 8B.
Figure 8B:
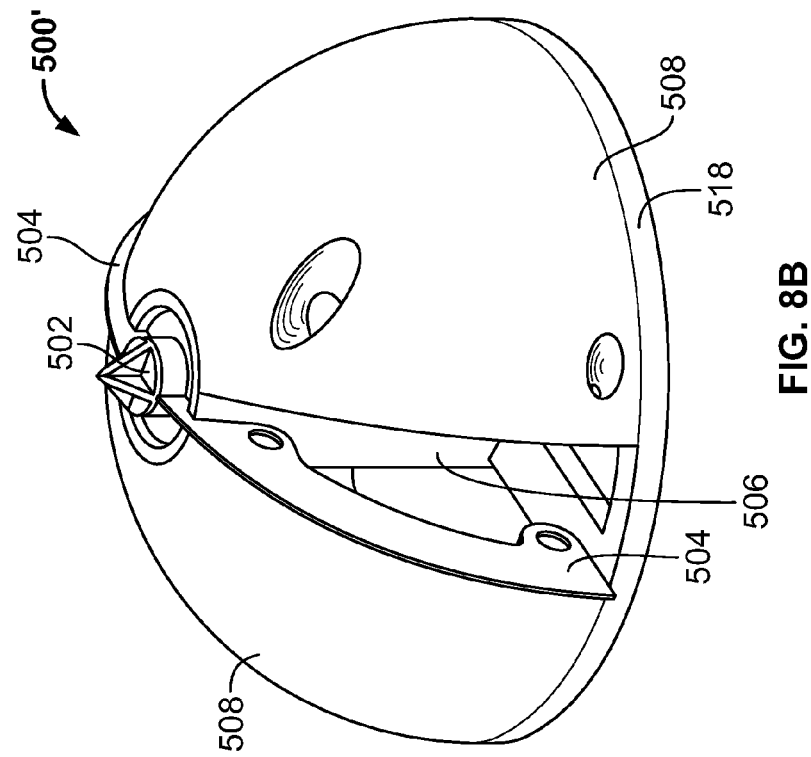
FIG. 8B is a stylized perspective view of a reamer for guided reaming according to the present teachings.

Referring to FIG. 8A, a reamer 500 can be guided along the alignment axis A to ream the acetabulum 82. Another embodiment of a reamer 500' according to the present teachings is illustrated in FIGS. 8B and 8C. The reamers 500 and 500' can be used interchangeably and similar elements will be referenced with the same numerals herein below. The reamer 500 (500') can include a trocar or other guiding pin 502 that is sized to fit and be received in the pilot hole 89 of the acetabulum 82 for stabilizing and guiding the reamer 500 (500') along the alignment axis A, i.e., at a predetermined location and orientation. This guided reaming arrangement enables the surgeon to recreate the preoperative planned position and orientation for reaming the acetabulum 82 and implanting the acetabular component. The alignment rod 402 which is supported by the support device 400 along the axis A' that is parallel to the alignment axis A can also help to guide the reamer 500 (500').

The reamer 500 (500') can include a plurality of curved reaming blades 504 and a supporting shaft 506 for a reamer driver or reamer handle. The curved blades 504 can be attached to a plurality of curved supporting elements 508 in the form of spherical leaves or spherical section/portions that collectively define a semi-spherical surface corresponding to the shape and size of the acetabular component to be implanted in the acetabulum after reaming. The blades 504 can be removable and replaceable or disposable. The entire reamer head that includes the blades 504 and the support element 508 can also be disposable. A reamer 500 with four disposable blades 504 is illustrated in FIG. 8A, while the reamer 500' shown in FIGS. 8B and 8C includes only two reamer blades 504. Referring to FIG. 8C, the guiding pin 502 can be spring biased to provide a tactile feedback during reaming. A spring or other biasing element 510 can be constrained between a proximal end 512 of the guiding pin 502 and a wall 514 of the supporting shaft 506. A set screw or fastener 516 can be used to stabilize the guiding pin 502 while allowing slidable movement along the alignment axis during reaming. The spring 510 can surround the fastener 516, as shown in FIG. 8C. Specifically, the fastener 516 is threaded to a blind bore 503 of the guiding pin 502 such that the fastener 516 and the guiding pin can move together along the alignment axis A by or against the action of the spring 510. The embodiments of FIGS. 8B and 8C also include a base ring 518 integrally attached to the shaft 506 providing additional stability.

Figure 9:
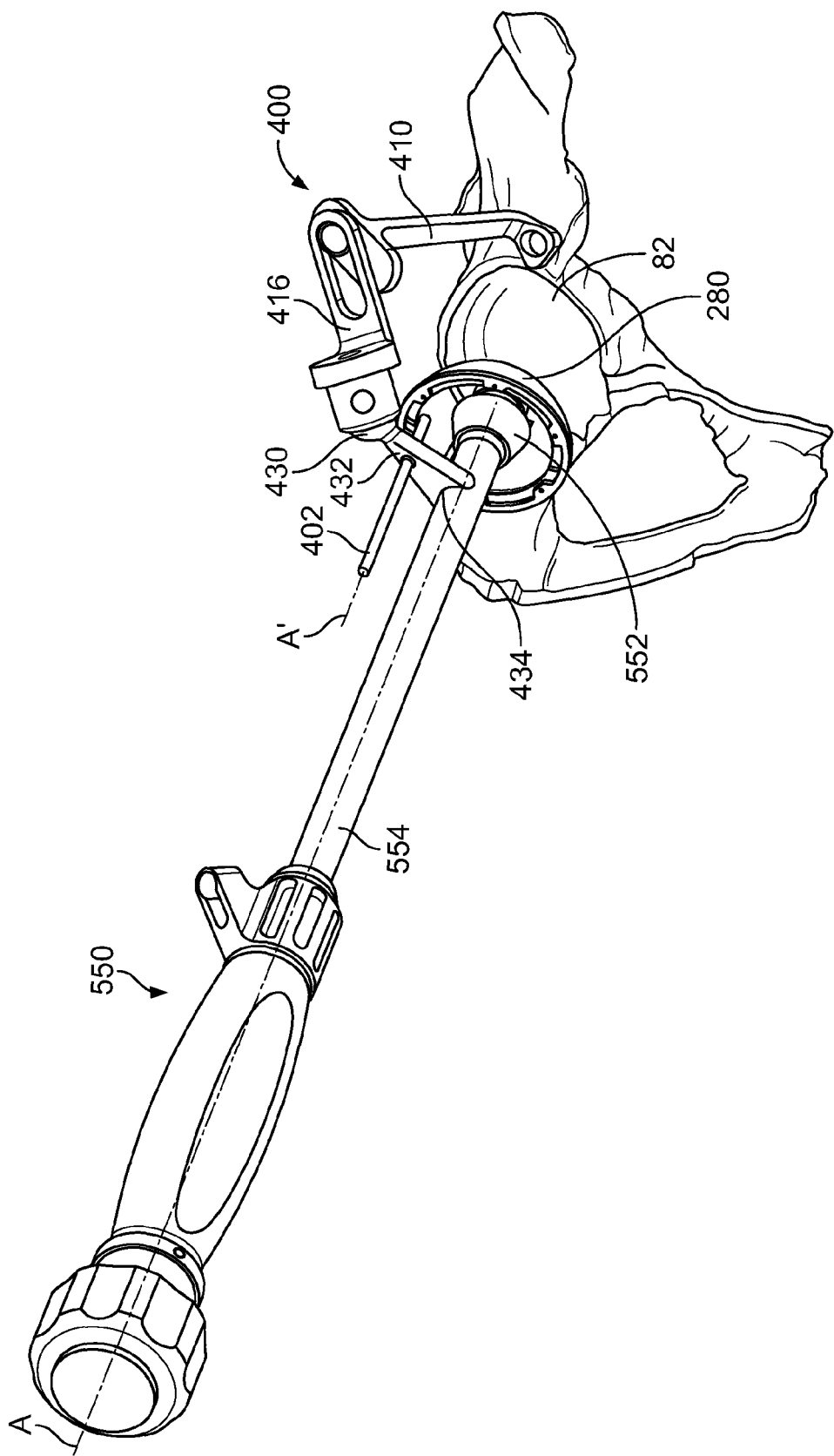
FIG. 9 is an environmental perspective view illustrating instruments for cup insertion according to the present teachings.
Figure 11:
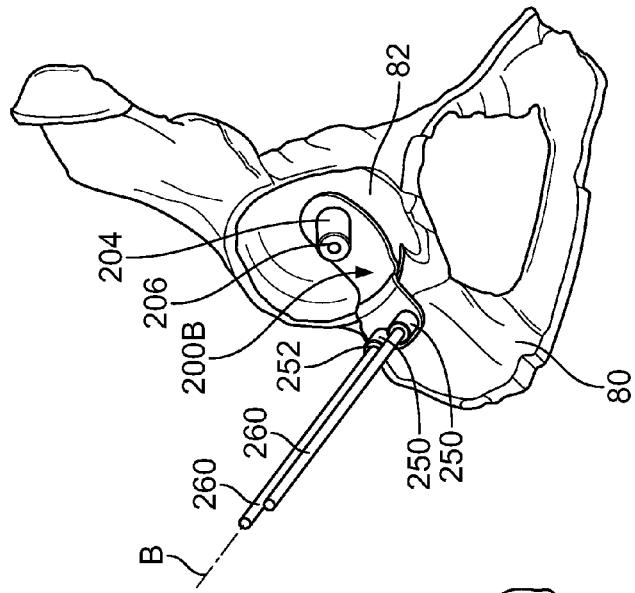
FIG. 11 is an environmental perspective view of another patient-specific acetabular alignment guide with alignment pins for a secondary guide according to the present teachings.

Referring to FIG. 9, after the acetabulum 82 has been reamed an acetabular inserter 550 can be coupled to an acetabular cup 280 by an end coupler 552 at the distal end of a shaft 554 of the acetabular inserter 550. The end coupler 552 can be removable. As seen in FIG. 9, the shaft 554 can be slidably and removably coupled to the engagement surface 434 of the connector 432 of the support device 400, such that the shaft is oriented along the alignment axis A for insertion of the acetabular cup 280 according to the preoperatively planned position and orientation.

Referring to FIGS. 10-13, another method of reaming and preparing the acetabulum 82 is illustrated using the acetabular guides 200 with fitment options 200A and 200B, as described above in connection with FIGS. 4 and 5. In this method, marker pins 260 are inserted through the corresponding bores 252 of the marker elements 250 and attached to the bone in locations and orientations parallel to an axis B, as determined during the preoperative plan. The marker pins 260 can guide the location of a secondary guide 600, shown in FIG. 13, which is designed according to the pre-operative plan to be guided by the marker pins 260, as discussed below.

As was described above in connection with FIG. 7 and the acetabular guides 100, a pilot hole 89 is drilled into the acetabulum 82 through the guiding element 204 with a drilling element 440 until the stop 442 of the drilling element 440 reached the upper surface of the guiding element 204 of the acetabular guide 200. The acetabular guide 200 can be slidably lifted off the marker pins 260 and removed, leaving the marker pins 260 attached to the bone. A reamer 500, 500' with a guiding pin 502 can be used to ream the acetabulum 82, as discussed above in connection with FIG. 7. The acetabular cup 280 can be inserted using an acetabular inserter 550 without the aid of an alignment orientation, although a support device 400 with an alignment rod 402 can also be used if desired.

After the acetabular cup 280 is inserted but not impacted, a secondary guide 600 having guiding elements 650 with bores 652 complementarily corresponding to the orientation and relative location of the marker elements 250 of the acetabular guide 200 is placed over the marker pins 260. The secondary guide 600 can be designed during the pre-operative plan such that the bores 652 are complementary to the location and orientation of the marker elements 250 of the acetabular guide. The secondary guide 600 can include extender elements 604 supporting an arcuate or crescent-shaped planar flange 602 having parallel inferior and superior surfaces 608, 610 designed during the pre-operative plan to be oriented parallel to a rim 282 of the acetabular cup 280, when the acetabular cup 280 is positioned in the predetermined position and orientation. The orientation and position of the acetabular cup 280 is adjusted using the secondary guide 600, such that the planar flange 602 (and the inferior and superior surfaces 608, 610 of the planar flange 602) and the rim 282 are parallel. It is noted that this method does not make use of the support device 400, although the acetabular guides 200 can also be used with the supporting device, at the discretion of the surgeon. Depending on the surgeon's preferences, any selected or all the acetabular guides 100 (110A, 100B, 100C) and 200 (200A, 200B) and the associated instruments including the reamer 500, 500', the supporting device 400, the drilling element 440 with the stop 442, alignment rod 402, marker pins 260 and the secondary guide 600 can be provided in a surgical kit together with the acetabular cup 280 and/or additional implants and instruments.

Figure 15A:
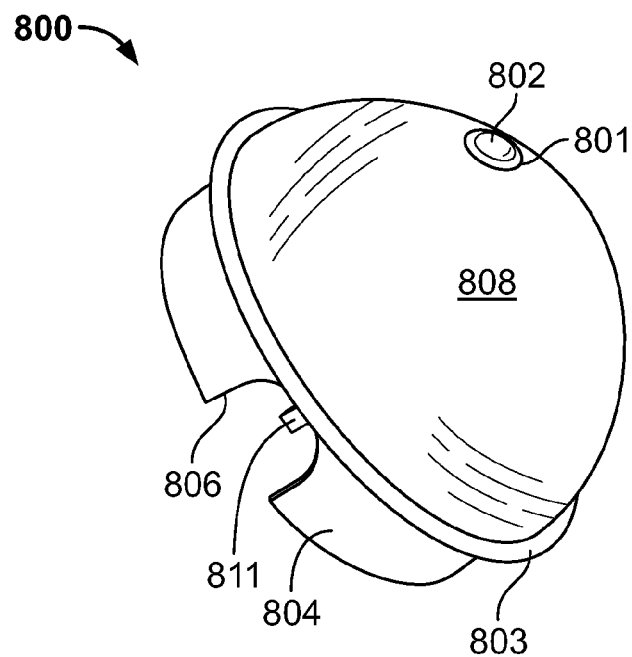
FIG. 15A is a perspective view of the orientation device of FIG. 14.
Figure 15B:
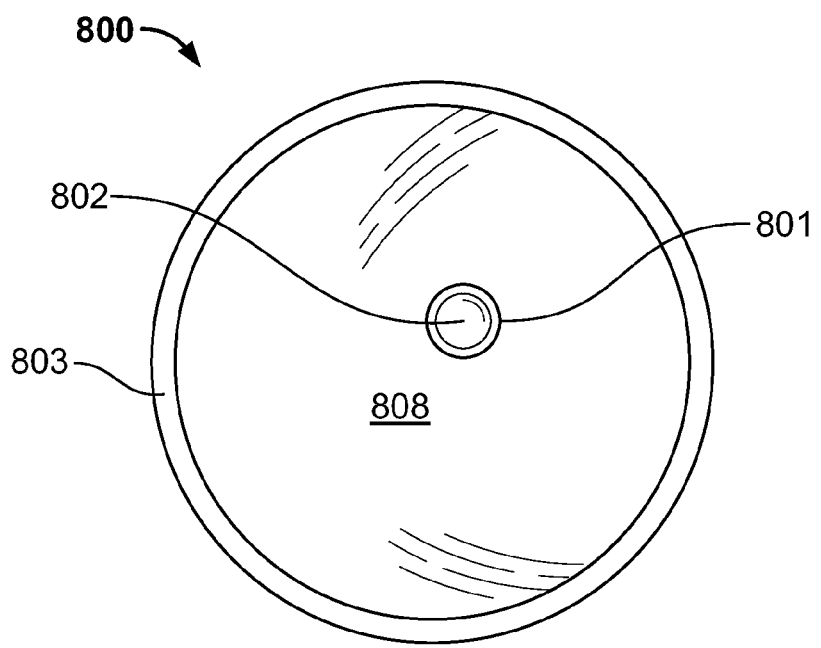
FIG. 15B is a plan view of the orientation device of FIG. 14.

Referring to FIGS. 15A and 15B, an orientation device 800 can be used to establish the alignment axis A for preparing a joint surface with a cutting tool and inserting an implant along the alignment axis. The cutting tool can be a milling, reaming, resurfacing, burring, sawing or any other tool for preparing the joint surface of the patient. The joint can be a hip, knee, elbow, shoulder or other joint surface.

Figure 16:
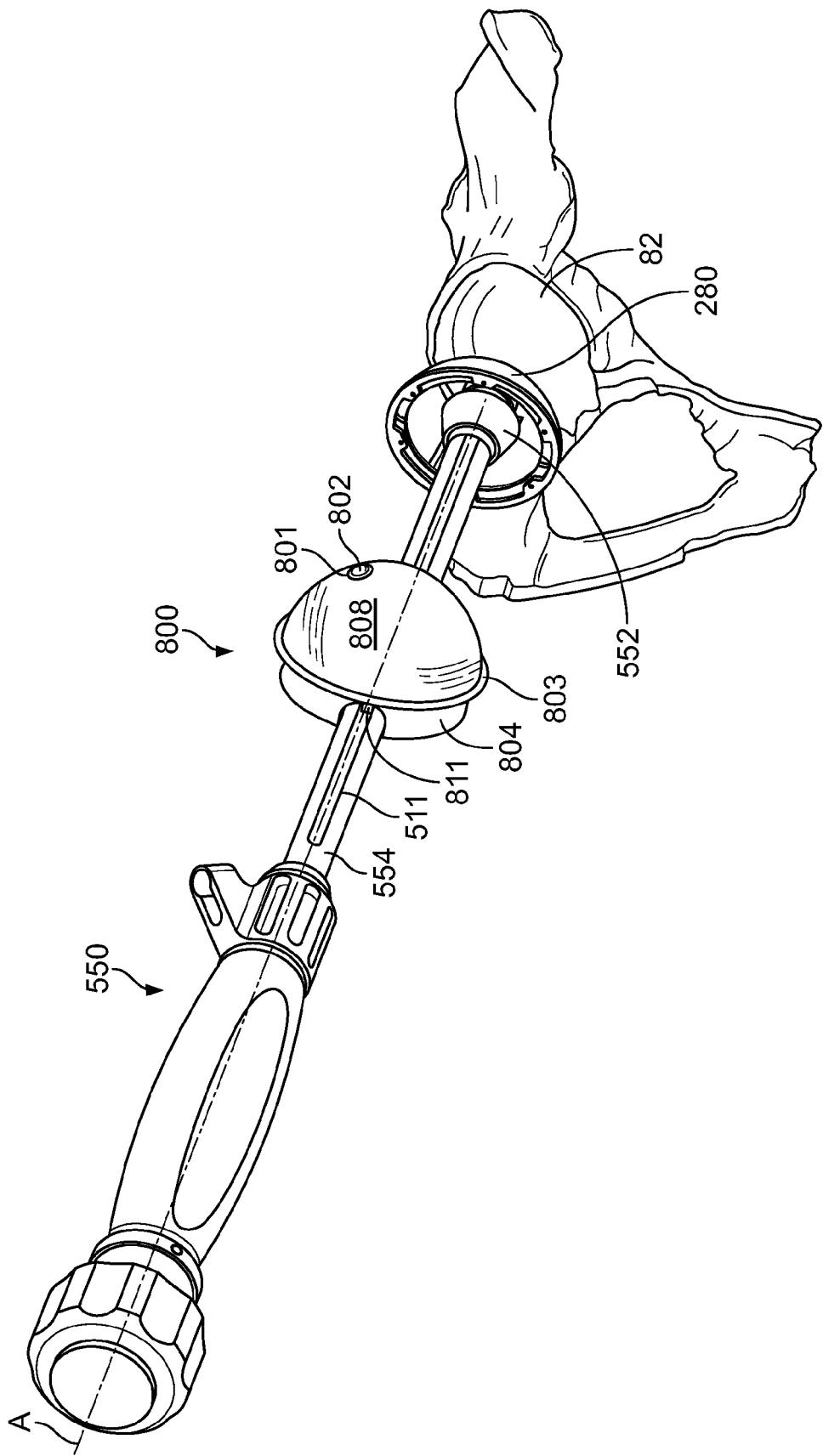
FIG. 16 is an environmental perspective view illustrating a method for inserting an acetabular cup using the orientation device of FIG. 15A according the present teachings.
Figure 17:
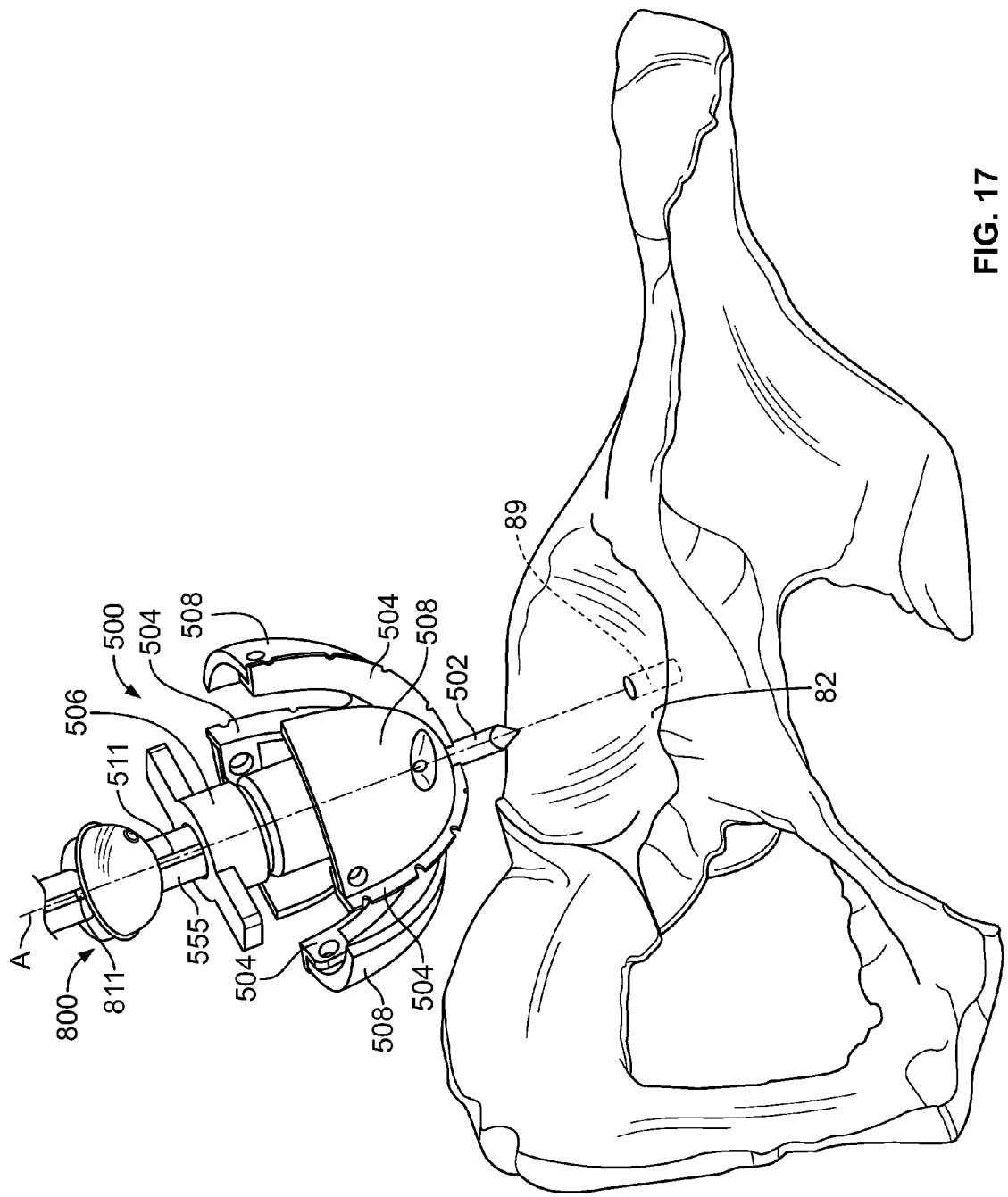
FIG. 17 is an environmental perspective view illustrating a method for preparing an acetabulum using the orientation device of FIG. 15A according the present teachings.

Referring to FIGS. 14-17, the orientation device 800 is illustrating in exemplary procedures for reaming the acetabulum 82 and inserting an acetabular cup 280. The orientation device 800 can be designed to indicate whether an axis of a shaft (304, 554, 555) or other longitudinal member of an instrument to be in preparation of the joint surface and/or insertion of the implant is aligned along a predetermined and patient-specific orientation when the orientation device 800 is attached to the longitudinal member. The longitudinal member can be a shaft of any surgical instrument including, for example, cutting/milling/reaming/burring tools, implant inserters and impactors. The orientation device 800 can also be attached any shaft that can be removably coupled to a modular tool. In the exemplary embodiments illustrating the use of the orientation device 800 for an acetabular joint surface, the longitudinal member can be the shaft 304 of the guiding handle 300 (FIG. 6, FIG. 14), the shaft 554 of the inserter 550 (FIG. 9, FIG. 16) or a shaft 555 coupled to a reamer 500 (FIG. 17). The shafts 304, 554 and 555 can be removably coupled to the respective instruments. In some embodiments, a single (the same) shaft can be used for more than one instrument.

Referring to FIGS. 15A and 15B, the orientation device 800 can be a three-dimensional leveling device having a three-dimensional orientation capability. For example, the orientation device 800 can include a transparent dome-shaped surface 808, such as a portion of a sphere or a hemisphere or a dome, attached to a planar base 803. The volume between the surface 808 and the planar surface can be filled with a liquid having a single air bubble or leveling bubble 802 to act as an orientation indicator. The shape of the orientation device 800 allows the bubble 802 to move in three-dimensional space indicating an orientation in three-dimensions relative to the base 803 and is a three-dimensional symmetric surface, such as a hemispherical surface. A coupler 804 can extend from the base 803 for removably coupling the orientation device to a shaft. The coupler 804 can include, for example, a snap-on groove 806 configured to removably attach to any one of the shafts 304, 554 and 555 as discussed above. The coupler 804 can be keyed to the shaft with a tongue-in-groove or other keying device. The keying device can include a first key component 811 on the coupler 803 and a second key component 311 on shaft 304 (511 on shafts 554 and 555) mating with the first key component 811. The first key component 811 can be an extension or tab or key and the second key component 311 or 511 can be a mating slot or channel or groove, or the other way around. The coupler 804 can be integrally or removably coupled to base 803. The coupler 804 can be attached to the base with adhesive, hoop-and-loop material, respective tongue-and-groove or deflectable snap-on elements or other connections. In some embodiments, the coupler 804 can be attachable to shafts with variable size diameters. Alternatively, a variety of removable couplers 804 having grooves 806 with different sizes can be provided for coupling to shafts of different diameters.

Figure 14:
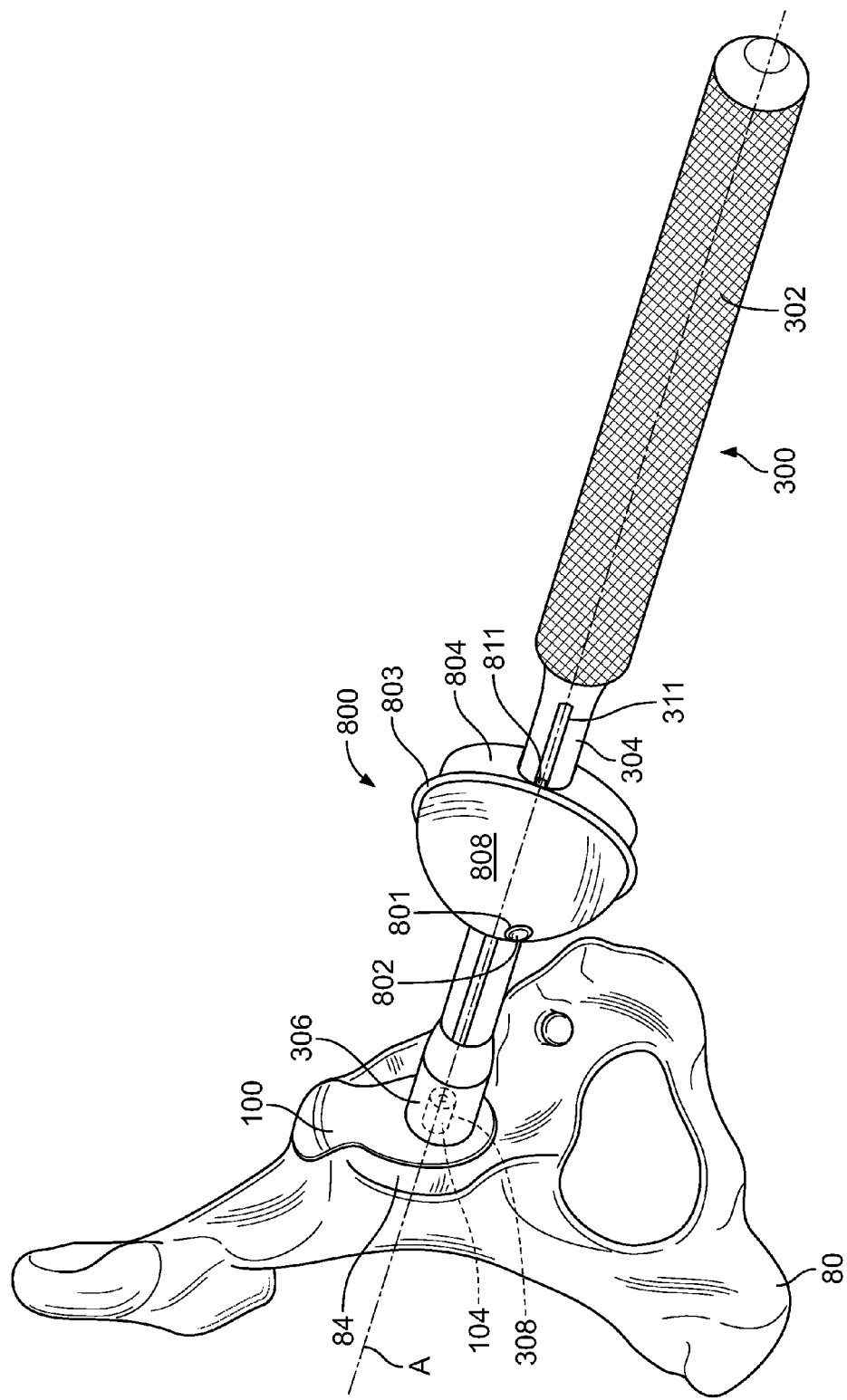
FIG. 14 is an environmental perspective view illustrating a method for establishing an acetabular cup insertion axis using an orientation device according to the present teachings.

The orientation device 800 can be calibrated using one of the patient specific acetabular guides 100 or 200, in any fitment option. Referring to FIG. 14, for example, a patient-specific acetabular guide is positioned in a unique location on the patient's acetabulum 82. The guiding element 104 of the acetabular guide 100 is oriented along the pre-operatively determined patient-specific alignment axis A, as discussed above in connection with FIGS. 1-5, for example. The guiding handle 300 (or the acetabular inserter 550 with the adapter tip 306, as discussed above) with the orientation device 800 keyed thereon is coupled and keyed to the guiding element 104 and the shaft 304 of the guiding handle 300 (or the acetabular inserter 550 with the adapter tip 306, as discussed above) becomes oriented along the same alignment axis A, as discussed above, in connection with FIG. 4. While the shaft 304 is oriented along the alignment axis A, the position of the bubble 802 is marked using a marker, pencil or other marking instrument with a mark 801, which can be, for example a dot at its center or a circle surrounding and centered about the bubble 802. When the orientation device 800 is subsequently attached and keyed to another shaft, that shaft can be aligned along the alignment axis A by ensuring that the bubble 802 aligns and is centered relative to the mark 801, as discussed below. Referring to FIGS. 16 and 17, the orientation device 800, can be used to align the shaft 554 of the inserter 550 and/or the shaft 555 of a reamer 500.

The orientation device 800 can be used with any of the methods discussed for preparing the acetabulum as an additional redundant alignment device, or with the following method. The orientation device 800 is first calibrated intra-operatively as discussed above in connection with FIG. 14. Specifically, the pre-selected patient-specific guide 100 is attached in a pre-operatively determined unique location relative to the acetabulum 82 of the specific patient. In this position, the guiding element 104 of the acetabular axis is oriented along the pre-operatively determined alignment axis A. The guiding handle 300 (or the acetabular inserter 550 with the adapter tip 306, as discussed above) with the orientation device 800 coupled and keyed thereon can be coupled to the acetabular guide 100 such that the guiding element 104 is received and keyed in the bore 308 of the distal portion 306 of the guiding handle 300 (or the acetabular inserter 550 with the adapter tip 306, as discussed above), thereby aligning the shaft 304 of the guiding handle 300 along the alignment axis A. The position of the bubble 802 relative to the base 803 is noted and a mark 801 is placed on the surface 808 centered relative to the bubble. The mark 801 can be made with a marker or other writing or marking instrument.

The guiding handle 300 (or the acetabular inserter 550 with the adapter tip 306, as discussed above) is removed from the acetabular guide 100. If a guiding handle 300 was used, then the orientation device 800 is removed from the guiding handle 300. If the acetabular inserter with the adapter tip 306 was used, then the orientation device 800 remains on the acetabular inserter 550, but the adapter tip 306 is removed and replaced with the end coupler 552, shown in FIG. 16. The acetabular guide 100 can be optionally used to drill a pilot hole 89 in the acetabulum 82, as discussed above, for example in connection with FIG. 7. Otherwise, the acetabular guide 100 is removed from the patient without drilling a pilot hole 89. A reamer, such as the reamer 500 discussed above in connection with FIG. 8A, for example, or other reamer can be used the ream the acetabulum 82 along the alignment axis A. More specifically, and referring to FIG. 17, a driver handle having a shaft 555 is coupled to the reamer 500. The orientation device 800 is connected to the shaft 555. The orientation of the shaft 555 is adjusted such that the orientation device 800 indicates alignment along the alignment axis A, i.e., the bubble 802 is centered relative to the mark 801. After reaming the acetabulum 82, the orientation device 800 can be attached to the shaft 554 of the inserter 500 for inserting the acetabular implant 280 into the prepared acetabulum 82, as shown in FIG. 16.

Although the orientation device 800 was described above in connection with an acetabular joint, the orientation device 800 can be used conveniently for aligning a variety of surgical instruments used during the preparation of any joint surface of a patient for receiving an implant in orthopedic surgery. It can provide alignment accuracy when calibrated with patient-specific guides that include guiding elements designed during a pre-operative plan for a specific patient. Several disposable or reusable orientation devices 800 with various patient-specific guides and guiding handles or modular shafts can be included in a surgical kit for a specific patient. For example, a number of orientation devices 800 can be included in a kit with one or more acetabular guides 100, 200 and other instruments that can be modularly coupled to the guiding elements 104, 204 of the acetabular guides for an acetabular joint replacement procedure. Guiding handles or other modular shafts, as well as reamers, inserters and other instruments and/or implant can also be included in the surgical kit. Marking instruments, such as off-the-shelf markers, disposable or other sterilizable markers can also be included. Implant components for the specific patient can also be included in the surgical kit.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. A method for preparing an acetabulum of a patient for an acetabular implant, the method comprising:
    removably engaging an acetabular area of the patient to a complementary surface of a patient-specific acetabular guide, the complementary surface of the patient-specific acetabular guide constructed as a mirror surface of the acetabular area from medical images of the patient obtained preoperatively, the acetabular guide having a guiding element oriented along a patient-specific alignment axis, the alignment axis determined during a preoperative plan of the patient for implant alignment;

removably coupling a shaft of a guiding tool to the guiding element of the acetabular guide such that the shaft of the guiding tool is oriented along the alignment axis;

removably attaching a three dimensional orientation device to the shaft of the guiding tool;

calibrating the orientation device to indicate the alignment axis orientation by marking with a mark a position of a bubble inside the orientation device, the bubble viewable through an outer transparent surface of the orientation device;

removing the acetabular guide and guiding tool;

removing the orientation device from the guiding tool;

removably attaching the orientation device to a shaft of an instrument; and determining the alignment axis by changing the orientation of the shaft such that the bubble of the orientation device is centered around the mark;

guiding the shaft of the instrument along the alignment axis using the orientation device.

2. The method of claim 1, wherein the instrument is a reamer and further comprising reaming the acetabulum with the reamer.

3. The method of claim 2, further comprising:
removing the orientation device from the shaft of the reamer;
removably attaching the orientation device to a shaft of an inserter coupled to an acetabular cup;
guiding the shaft of the inserter along the alignment axis using the orientation device; and
inserting the acetabular cup in the acetabulum.

4. The method of claim 2, further comprising:
drilling a pilot hole in the acetabulum through a bore of the guiding element; and
guiding an alignment pin of the reamer in the pilot hole.

5. The method of claim 4, wherein drilling a pilot hole in the acetabulum through a bore of the guiding element includes using a drilling element having a stop at a predetermined position for preventing overdrilling of the acetabulum.

6. The method of claim 1, further comprising keying the orientation device to the shaft of the instrument.

7. The method of claim 1, wherein the guiding tool is a guiding handle.

8. The method of claim 1, wherein the guiding tool is an acetabular inserter with a removable adapter tip couplable to the guiding element of the patient-specific acetabular guide.

9. The method of claim 1, wherein the orientation device includes a transparent dome-shaped surface and a base.

10. The method of claim 9, further comprising coupling the base of the orientation device to the shaft of the guiding tool with a coupler extending from the base.

11. A method for preparing a joint surface of a patient for an implant, the method comprising:
attaching a surface of a patient-specific guide to a complementary joint surface of the patient, the surface of the patient-specific guide constructed as a mirror surface of the complementary joint surface from medical images of the patient obtained preoperatively, the patient-specific guide having a guiding element oriented along a patient-specific alignment axis, the alignment axis determined during a preoperative plan of the patient for implant alignment;

removably coupling a shaft of a guiding tool to the guiding element of the patient-specific guide;

removably attaching a three-dimensional orientation device to the shaft of the guiding tool;

marking a position of a bubble of the orientation device with a mark on an outer transparent surface of the orientation device while the guiding tool is oriented along the alignment axis;

removing the orientation device from the guiding tool;

removing the patient-specific guide and the guiding tool;

removably attaching the orientation device to a reamer;

aligning the reamer along the alignment axis using the orientation device by changing the orientation of the reamer such that the bubble of the orientation device is centered around the mark; and reaming the joint surface.

12. The method of claim 11, further comprising:
keying the orientation device to a shaft of the reamer.

13. The method of claim 11, wherein the orientation device includes a transparent dome-shaped surface, a base and a coupler extending from the base.

14. A method for preparing a joint surface of a patient for an implant, the method comprising:
attaching a surface of a patient-specific guide to a complementary joint surface of the patient, the surface of the patient-specific guide constructed as a mirror surface of the complementary joint surface from medical images of the patient obtained preoperatively, the patient-specific guide having a guiding element oriented along a patient-specific alignment axis, the alignment axis determined during a preoperative plan of the patient for implant alignment;

removably coupling a shaft of a guiding tool to the guiding element of the patient-specific guide;

removably attaching a three-dimensional orientation device to the shaft of the guiding tool;

marking a position of a bubble of the orientation device with a mark on an outer transparent surface of the orientation device while the guiding tool is oriented along the alignment axis;

removably keying and attaching the orientation device to a shaft of an inserter holding an implant for the joint surface;

aligning the shaft of the inserter along the alignment axis using the orientation device by changing the orientation of the shaft of the inserter such that the bubble of the orientation device is centered around the mark; and inserting the implant in the joint surface.

15. The method of claim 14, wherein the inserter is an acetabular inserter with an adapter tip couplable to the guiding element of the patient-specific guide.

16. The method of claim 14, wherein the orientation device includes a transparent dome-shaped surface, a base and a coupler extending from the base.

* * * * *

UNITED STATES PATENT AND TRADEMARK OFFICE
CERTIFICATE OF CORRECTION

Page 1 of 1

PATENT NO. : 8,608,749 B2
APPLICATION NO. : 13/041469
DATED : December 17, 2013
INVENTOR(S) : Jason D. Meridew It is certified that error appears in the above-identified patent and that said Letters Patent is hereby corrected as shown below:

On the Title Page, References Cited, Other Publications, Column 2, line 59, (Information Disclosure Statement dated July 8, 2011, Form 1449, page 19, Non Patent Literature Documents, Reference No. CI2), Delete "Arthuroplasty" and insert --Arthroplasty--.

In the Specification

Column 3, Line 39; Before "the", insert --to--.

Column 3, Line 42; Before "the", insert --to--.

Column 6, Line 2; Delete "1008" and insert --100B--.

Column 7, Line 18; Delete "100" and insert --200--.

Column 8, Line 11; Before "a", insert --of--.

Column 8, Line 33; Before "is", delete "and".

Signed and Sealed this
Nineteenth Day of August, 2014

Michelle K. Lee
*Deputy Director of the United States Patent and Trademark Office*